(12) United States Patent
Van Den Bosch et al.

(10) Patent No.: US 9,238,028 B2
(45) Date of Patent: Jan. 19, 2016

(54) HDAC INHIBITORS TO TREAT CHARCOT-MARIE-TOOTH DISEASE

(71) Applicants: VIB VZW, Ghent (BE); Life Sciences Research Partners VZW, Leuven (BE)

(72) Inventors: Ludo Van Den Bosch, Arendonk (BE); Constantin Van Outryve d'Ydewalle, Bruges (BE); Wim Robberecht, Kumtich (BE)

(73) Assignees: VIB VZW, Gent (BE); Life Sciences Research Partners VZW, Leuven (BE)

( * ) Notice: Subject to any disclaimer, the term of this patent is extended or adjusted under 35 U.S.C. 154(b) by 0 days.

(21) Appl. No.: 14/335,716

(22) Filed: Jul. 18, 2014

(65) Prior Publication Data

US 2014/0329849 A1 Nov. 6, 2014

Related U.S. Application Data

(63) Continuation of application No. 13/877,648, filed as application No. PCT/EP2011/067438 on Oct. 6, 2011.

(60) Provisional application No. 61/404,796, filed on Oct. 8, 2010.

(51) Int. Cl.
*A61K 31/437* (2006.01)
*A61K 31/422* (2006.01)
*A01K 67/027* (2006.01)

(52) U.S. Cl.
CPC ........... *A61K 31/437* (2013.01); *A01K 67/0275* (2013.01); *A61K 31/422* (2013.01)

(58) Field of Classification Search
CPC ... A61K 31/422; A61K 31/437; A61K 31/38; A61K 31/4375; A01K 67/0275; C07D 207/34; C07D 215/54; C07D 261/18; C07D 277/56; C07D 401/04; C07D 401/06
USPC ................................................. 514/292, 376
See application file for complete search history.

(56) References Cited

U.S. PATENT DOCUMENTS

| | | | |
|---|---|---|---|
| 7,244,853 B2 | 7/2007 | Schreiber et al. | |
| 7,737,175 B2 | 6/2010 | Yao et al. | |
| 2004/0072735 A1* | 4/2004 | Richon et al. | 514/9 |
| 2008/0312175 A1* | 12/2008 | Yao et al. | 514/44 |
| 2013/0227717 A1 | 8/2013 | Van Den Bosch et al. | |

FOREIGN PATENT DOCUMENTS

| WO | 2007/061939 | 5/2007 |
|---|---|---|
| WO | WO/2007/061939 | * 5/2007 |
| WO | 2007/130419 | 11/2007 |
| WO | WO/2007/130419 | * 11/2007 |
| WO | 2011/091213 | 7/2011 |
| WO | 2012/045804 A1 | 4/2012 |

OTHER PUBLICATIONS

,Vasilescu et al Journal of Neurological Science, 1984, 63, 11-25.*
Legace et al The Journal of Biological, 2004, 279, 18, 18851-18860.*
Kazantsev et al Nature review, 2008, 854-868.*
Houlden et al Neurology, 2008; 71: 1660-1668.*
Kijima et al J Hum Genet (2005) 50: 473-476.*
Reed et al Curr Biol., 2006, 16:2166-2172.*
Dompierre et al The Journal of Neuroscience, Mar. 28, 2007 27(13):3571-3583.*
Chevalier-Larsen Biochimica et Biophysica Acta 1762 (2006) 1094-1108.*
Vasilescu C et al., Neuronal type of Charcot-Marie-Tooth Disease with a syndrome of continuous motor unit activity, Journal of Neurological Sciences, Jan. 1, 1984, pp. 11-25, vol. 63, No. 1, Elsevier Scientific Publishing Co., Amsterdam, NL.
D-Ydewalle C et al., A transgenic animal model for Charcot-Marie-Tooth disease caused by mutations in HSPB1 shows length-dependent muscle weakening and atrophy due to axonal loss, Society for Neurosciecnce Abstract Viewer and Itinerary Planner, 2009, vol. 39.
Butler K et al., Rational Design and Simple Chemistry Yield a Superior, Neuroprotective HDAC6 Inhibitor, Tubastatin A, Journal of American Chemical Society, Aug. 11, 2010, pp. 1042-1046, Vo. 132, No. 31.
PCT International Search Report, PCT/EP2011/067438 dated Mar. 27, 2012.
Rosenberg, G., The mechanisms of action of valproate in neuropsychiatric disorders: can we see the forest for the trees?, Cell. Mol. Life Sci., Review, 2007, pp. 2090-2103, vol. 64.
Khan et al., Determination of the class and isoform selectivity of small-molecule histone deacetylase inhibitors, Biochem. J., 2008, pp. 581-589, vol. 409.
Haggarty et al., Domain-selective small-molecule inhibitor of histone deacetylase 6 (HDAC6)-mediated tubulin deacetylation, PNAS, Apr. 15, 2003, pp. 4389-4394, vol. 100, No. 8.
Furumai et al., FK228 (Depsipeptide) as a Natural Prodrug That Inhibits Class I Histone Deacetylases, Cancer Research, Sep. 1, 2002, pp. 4916-4921, vol. 62.
Gottlicher et al., Valproic acid defines a novel class of HDAC inhibitors inducing differentiation of transformed cells, The EMBO Journal, 2001, pp. 6969-6978, vol. 20, No. 24.
Phiel et al., Histone Deacetylase Is a Direct Target of Valproic Acid, a Potent Anticonvulsant, Mood Stabilizer, and Teratogen, The Journal of Biological Chemistry, Sep. 28, 2001, pp. 36734-36741, vol. 276, No. 39.
Legace et al., The Journal of Biological, 2004, 279, 18, 18851-18860.
Houlden et al., Neurology, 2008, 71, 1660-1668.
Kijima et al., J. Hum Genet, 2005, 50, 473-476.

* cited by examiner

*Primary Examiner* — Anoop Singh
(74) *Attorney, Agent, or Firm* — TraskBritt, P.C.

(57) ABSTRACT

The disclosure relates to diseases in the peripheral nervous system, particularly hereditary neuropathies, such as Charcot-Marie-Tooth (CMT) disease. It is shown that this disease is associated with decreased acetylated tubulin levels, which can be overcome by inhibition of histone deacetylases (HDACs). Using HDAC inhibitors, it is shown herein that the symptoms of the CMT phenotype can be overcome both in vitro and in vivo. Also provided herein are two different mouse models of CMT disease.

2 Claims, 13 Drawing Sheets
(10 of 13 Drawing Sheet(s) Filed in Color)

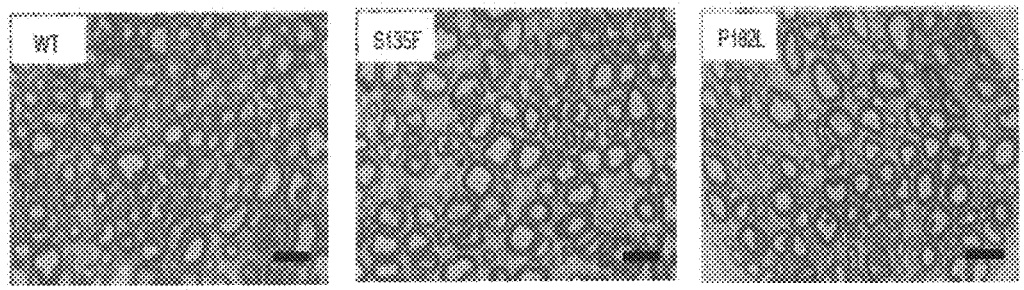
FIG. 4G
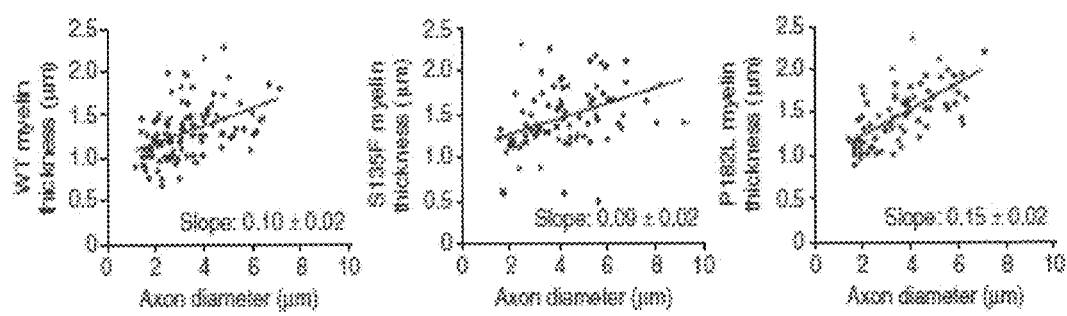
FIG. 4H
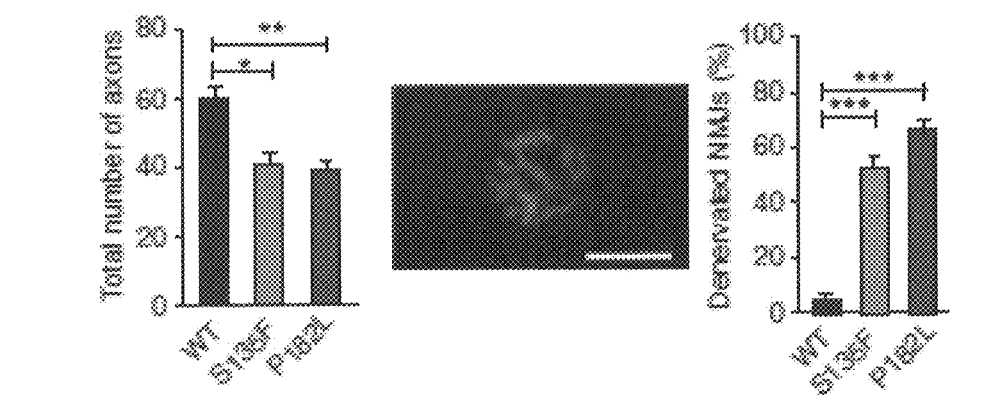
FIG. 4I                    FIG. 4J

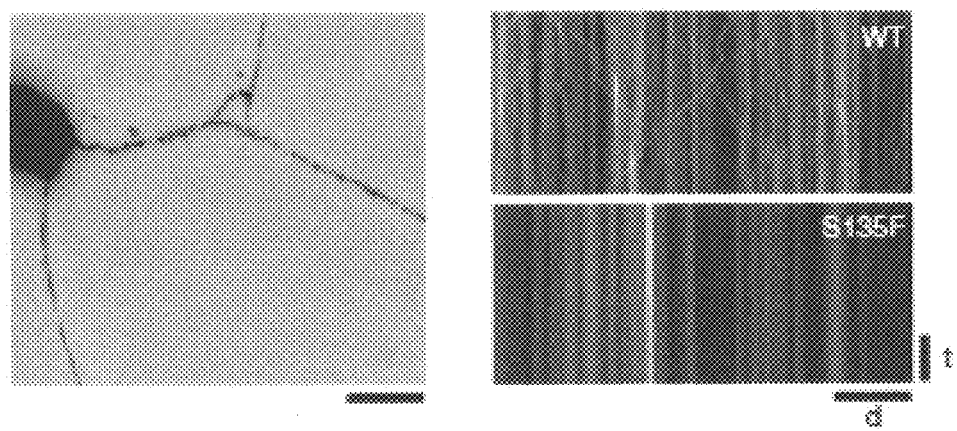
FIG. 6A
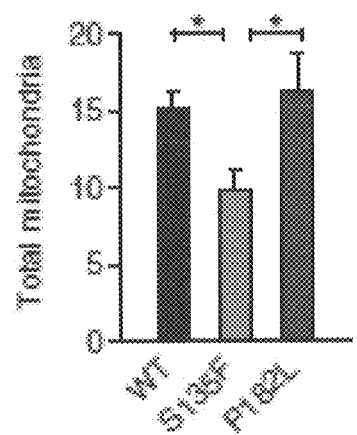 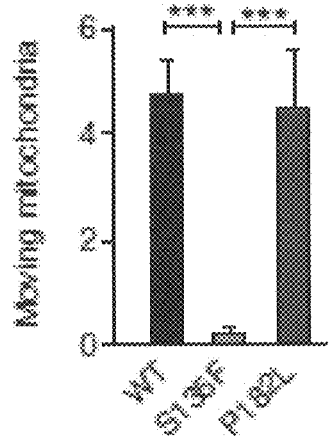
FIG. 6B  FIG. 6C
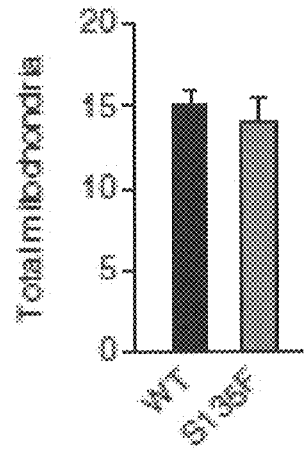 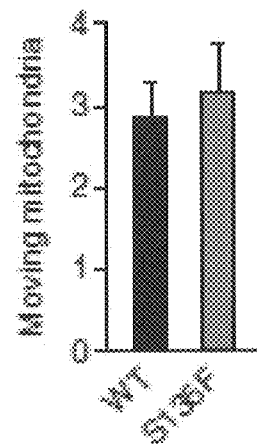
FIG. 6D  FIG. 6E

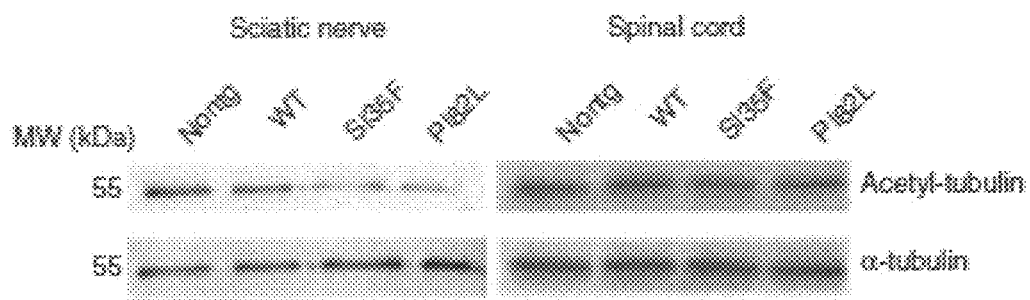
FIG. 6F
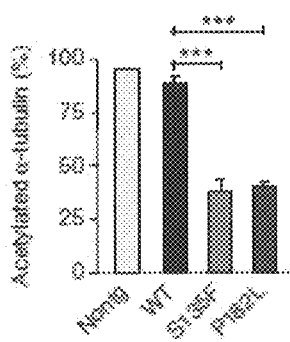 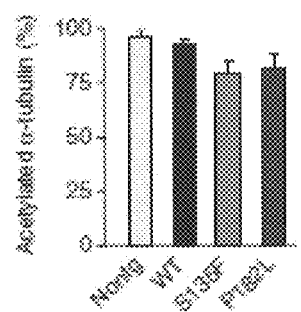 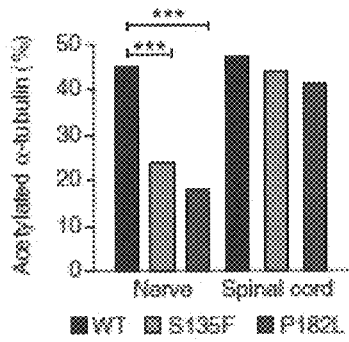
FIG. 6G  FIG. 6H  FIG. 6I

FIG. 8A 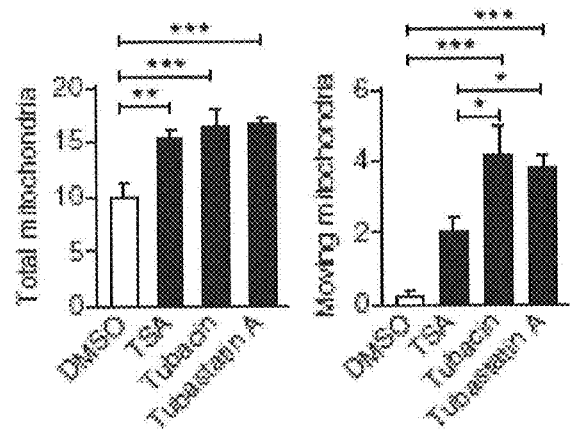 FIG. 8B

FIG. 8E 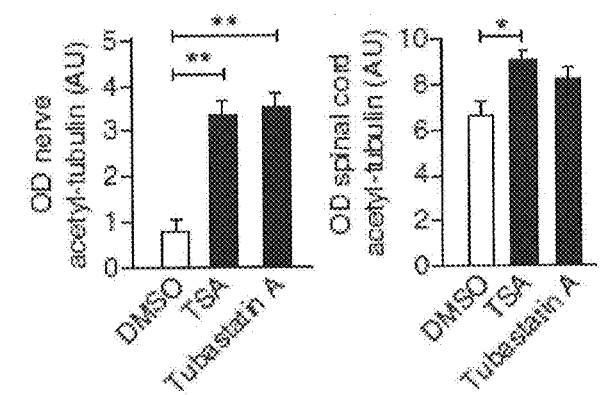 FIG. 8F

FIG. 8G  FIG. 8H

HDAC INHIBITORS TO TREAT CHARCOT-MARIE-TOOTH DISEASE

CROSS-REFERENCE TO RELATED APPLICATIONS

This application is a continuation of co-pending U.S. patent application Ser. No. 13/877,648, filed Apr. 3, 2013, which application is a national phase entry under 35 U.S.C. §371 of International Patent Application PCT/EP2011/067438, filed Oct. 6, 2011, designating the United States of America and published in English as International Patent Publication WO 2012/045804 A1 on Apr. 12, 2012, which claims the benefit under Article 8 of the Patent Cooperation Treaty and under 35 U.S.C. §119(e) to United States Provisional Patent Application Ser. No. 61/404,796, filed Oct. 8, 2010, the disclosure of each of which is hereby incorporated herein in its entirety by this reference.

TECHNICAL FIELD

The disclosure relates to diseases in the peripheral nervous system, particularly hereditary neuropathies, most particularly, Charcot-Marie-Tooth (CMT) disease. It is shown that this disease is associated with decreased acetylated tubulin levels, which can be overcome by inhibition of histone deacetylases (HDACs). Using HDAC inhibitors, it is shown herein that the symptoms of the CMT phenotype can be overcome both in vitro and in vivo. Also provided herein are two different mouse models of CMT disease.

BACKGROUND

Charcot-Marie-Tooth (CMT) disease affects approximately one in 2500 individuals and is the most common inherited disorder of the peripheral nervous system.[1,2] Clinically, CMT patients show slowly progressive distal muscle weakness and atrophy, foot deformities, steppage gait, distal sensory loss, and decreased or absent deep tendon reflexes.[1,2] Electrophysiologically, CMT is divided into three groups: demyelinating CMT (type 1), CMT characterized by axonal loss (type 2), and intermediate forms demonstrating signs of both demyelination and axonal loss. In cases where the disease exclusively affects motor axons and sensory involvement is absent, both clinically and electrophysiologically, the condition is referred to as distal Hereditary Motor Neuropathy (distal HMN). Thus far, CMT and distal HMN have been associated with approximately 40 causative genes (for an overview, see the World Wide Web at molgen.ua.ac.be/CMT-Mutations) and the pattern of inheritance can be autosomal dominant, autosomal recessive or X-linked.[1,2] The underlying pathological mechanism for most of the mutated genes remains unknown.

Mutations in the gene encoding the 27 kDa small heat-shock protein (HSPB1, also called HSP27) on chromosome 7q11.23 were previously identified as a cause of CMT2 and/or distal HMN2.[3,4] HSPB1 is a member of the small heat-shock proteins that contain a highly conserved α-crystallin domain. HSPB1 shows chaperone activity by binding to misfolded and/or (partially) denatured proteins and preventing them from forming toxic aggregates.[5,6] In addition, HSPB1 also plays a crucial role in diverse cellular processes such as modulation of the intracellular redox state, the assembly of cytoskeletal structures, cell differentiation, and inhibition of apoptosis by interacting with pro-apoptotic signaling proteins.[5-7]

So far, eleven missense mutations have been identified in HSPB1 that are all associated with CMT2 and/or distal HMN. Seven of these mutations are located in the α-crystallin domain (including S135F), two in the N-terminal part and two targeting the same amino acid (P182L/S) in the short C-terminal tail of the protein.[3,8-11] All these mutations are inherited autosomal dominantly, except one (L99M) that shows an autosomal recessive pattern of inheritance.[3,8-11] Depending on the mutation, patients show either CMT2 or distal HMN symptoms. The S135F mutation is the only one that causes both CMT2 and distal HMN.[3] Thus far, there is no cure for CMT disease, and any possible therapy would be most welcomed.

SUMMARY OF THE DISCLOSURE

Charcot-Marie-Tooth (CMT) disease is the most common inherited disorder of the peripheral nervous system. Mutations in the 27 kDa small heat-shock protein (HSPB1) cause axonal CMT or distal hereditary motor neuropathy (distal HMN). We developed and characterized transgenic mice expressing two different HSPB1 mutations (S135F and P182L) in neurons only. These mice show all features of CMT or distal HMN dependent on the mutation expressed. Expression of mutant HSPB1 decreased acetylated α-tubulin levels and induced severe axonal transport deficits. Pharmacological inhibition of histone deacetylase 6 (HDAC6)-induced α-tubulin deacetylation corrected the axonal transport defects induced by HSPB1 mutations and rescued the CMT phenotype of symptomatic mutant HSPB1 mice. The findings demonstrate the pathogenic role of α-tubulin deacetylation in mutant HSPB1-induced neuropathies and offers perspectives for HDAC6 inhibitors as a therapeutic strategy against hereditary axonopathies (see also d'Ydewalle et al., Nat. Med. 2011; 17(8):968-74; ref. 47), but also against induced peripheral neuropathies, such as chemotherapy-induced peripheral neuropathy.

Accordingly, provided are methods of treating neuropathies wherein acetylated α-tubulin levels are decreased, by increasing the levels of acetylated α-tubulin, thereby rescuing axonal transport defects. One way of increasing the levels of acetylated α-tubulin is by inhibiting histone deacetylase 6 (HDAC6), as this enzyme is known to deacetylate α-tubulin. This can be achieved using a selective HDAC6 inhibitor, such as tubacin or tubastatin A, a selective type II HDAC inhibitor, a less specific HDAC inhibitor or even a pan-HDAC inhibitor. (Note that an equivalent way of saying that methods are provided herein to treat neuropathies by administering a HDAC inhibitor to a subject in need thereof is to say that HDAC inhibitors, particularly HDAC6 inhibitors, are provided for use in treatment of neuropathies. It is to be understood that this applies to the other methods described herein as well, and the equivalent phrasing will thus not always be repeated.)

Although the findings presented herein are applicable to all kinds of diseases involving decreased acetylated α-tubulin levels, particularly envisaged is treatment of axonopathies or neuropathies, most particularly peripheral neuropathies, such as those involving mutated HSPB1. One of the envisaged neuropathies is Charcot-Marie-Tooth disease, particularly CMT type 2 (also known as axonal CMT) or distal HMN. Surprisingly, it is demonstrated herein that the phenotype of CMT, caused by axonal loss and muscle denervation, is reversed. Without being bound to a particular mechanism, it could be shown that HDAC inhibition resulted in regrowth of functional neurons, resulting in improved motor performance.

In particular embodiments, the methods of treating Charcot-Marie-Tooth disease by inhibiting HDAC function, particularly HDAC6 function, are used to treat Charcot-Marie-Tooth disease characterized by at least one mutation in the HSPB1 gene or protein. In further particular embodiments, the mutation in the HSPB1 gene or protein is a mutation in the alpha-crystallin domain of HSPB1, particularly of residue S135, most particularly a S135F point mutation. In alternative embodiments, the mutation in the HSPB1 gene or protein is a mutation in the C-terminal tail of HSPB1, particularly of residue P182, most particularly, a P182L point mutation.

In other particular embodiments, the HDAC function can be inhibited by using or administering a HDAC inhibitor, such as a pan-HDAC inhibitor, a non-selective inhibitor of type II HDACs, a selective inhibitor of type II HDACs, a selective inhibitor of type IIb HDACs or a selective inhibitor of HDAC6. In specific embodiments, the selective HDAC6 inhibitor is selected from tubacin and tubastatin A.

It is particularly envisaged that the methods of treating Charcot-Marie-Tooth disease by inhibiting HDAC function result in improvement of at least one of the symptoms of Charcot-Marie-Tooth disease, particularly an improvement in motor function. Alternatively, the methods provided herein result in reinnervation, i.e., in the growth of new, functional axons in the place of axons that were lost as result of the neuropathy.

In a further aspect, non-human transgenic animal models are provided that can serve as a model to study CMT disease. In particular embodiments, these animals are mice.

In other particular embodiments, the transgenic non-human animals are characterized by at least one mutation in the HSPB1 gene. In further embodiments, the mutation is neuron-specific.

In specific embodiments, the at least one mutation in the HSPB1 gene or protein is a mutation in the alpha-crystallin domain of HSPB1, particularly of residue S135, most particularly, a S135F point mutation. In alternative specific embodiments, the mutation in the HSPB1 gene or protein is a mutation in the C-terminal tail of HSPB1, particularly of residue P182, most particularly, a P182L point mutation.

In particular embodiments, the non-human transgenic animal models recapitulate at least one of the symptoms of Charcot-Marie-Tooth disease observed in humans.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Western blots of sciatic nerve, DRG, spinal cord and brain homogenates isolated from two-month-old non transgenic (Nontg) mice or mice expressing WT or mutant (S135F or P182L) HSPB1 probed with an antibody to the HA tag of the 27-kDa human HSPB1. Glyceraldehyde-3-phosphate dehydrogenase (Gapdh) staining confirmed equal loading. MW, molecular weight. FIG. 1B: Six-month-old mice expressing WT or mutant HSPB1 lifted by the tail showing normal spreading of the limbs (WT) or limb-clasping behavior (S135F and P182L). FIG. 1C: Monthly testing of the general motor performance of the different HSPB1-transgenic mice using an accelerating rotarod. n=25 mice per genotype. Two-way analysis of variance (ANOVA) for repeated measures. ***P<0.0001. FIGS. 1D and 1E: Age-dependent measurements of grip strength normalized to body weight of all paws combined (FIG. 1D) or forepaws only (FIG. 1E) using a dynamometer with a grid or a triangular bar, respectively. AU, arbitrary units. n=25 mice per genotype. Two-way ANOVA for repeated measures. Blue asterisks indicate differences between P182L and WT; red asterisks indicate differences between S135F and WT. The line represents the span in which data points are significantly different compared to WT. Tukey's HSD test was used for post hoc analysis. *P<0.05; ***P<0.0001. Data are presented as means±s.e.m.

FIGS. 4A-4J: Mutation-dependent pure motor or sensorimotor axonal loss and denervation of neuromuscular junctions in mice expressing mutant HSPB1. FIG. 4A: Relative difference in response latencies on a hot plate between mice expressing HSPB1$^{WT}$, HSPB1$^{S135F}$ and HSPB1$^{P182L}$. FIGS. 4B-4D: Determination of the amplitude and the latency of the CMAPs in mice expressing HSPB1$^{WT}$, HSPB1$^{S135F}$ or HSPB1$^{P182L}$. FIG. 4B: CMAP amplitudes as a function of age. FIG. 4C: Linear curve fitting of the CMAP data points ($R^2_{S135}$: 0.99 and $R^2_{P182L}$: 0.94). FIG. 4D: CMAP latencies as a function of age. FIGS. 4E and 4F: Age-dependent measurements of amplitudes (FIG. 4E) and latencies (FIG. 4F) of SNAPs. Blue asterisks indicate difference between P182L and WT. Red asterisks indicate difference between S135F and WT. Line represents the span in which the data points are significantly different compared to WT. Tukey's HSD test was used to analyze post hoc. FIG. 4G: Toluidine blue staining of semithin distal sciatic nerve sections of ten-month-old HSPB1$^{WT}$-expressing (left) and mutant HSPB1-expressing (middle and right) mice, showing axonal loss in the mutant lines. No signs of demyelination were observed. Scale bars, 40 μm. FIG. 4H: Correlation between myelin thickness and axonal diameter confirming the absence of demyelination in HSPB1$^{WT}$-expressing (left) and mutant HSPB1-expressing (middle and right) mice. FIG. 4I: Quantification of the number of axons in distal parts of the sciatic nerve. FIG. 4J: Left, example of a completely denervated neuromuscular junction stained with α-bungarotoxin (red) and negative for neurofilament heavy chain. Scale bar, 20 μm. Right, quantification of these denervated neuromuscular junctions in ten-month-old transgenic HSPB1 mice. In FIGS. 4A through 4F, n=15 mice per genotype. Two-way ANOVA for repeated measures was used in FIGS. 4A through 4F. One-way ANOVA was used in FIGS. 4G through 4J. FIGS. 4G through 4J, n=3 mice per genotype. *P<0.05;  P<0.001; * P<0.0001. Data are presented as means±s.e.m.

FIGS. 6A-6I: Mutant HSPB1 mice show axonal transport defects and decreased acetylated tubulin levels. FIG. 6A: Representative fluorescent micrograph of a cultured DRG neuron loaded with a selective mitochondrial marker (MitoTracker-Red; left) and typical kymographs obtained from DRG neurons isolated from ten-month-old mice (top right, HSPB1WT; bottom right, HSPB1S135F). Stationary mitochondria are visible as straight vertical lines, whereas moving mitochondria are deflected either to the left (retrograde) or to the right (anterograde). Left scale bar, 40 μm. In right images, time (t) scale bar: 50 seconds; distance (d) scale bar: 25 μm. FIGS. 4B through 4E: Quantification of total and moving (per 200 seconds and per 100 μm) mitochondria in DRG neurons isolated from different transgenic lines and at different ages. Total number (FIGS. 6B and 6D) and number of moving (FIGS. 6C and 6E) mitochondria were determined in DRG neurons from ten-month-old (FIGS. 6B and 6C) or two-month-old (FIGS. 6D and 6E) transgenic mice. n=25 to 35 cells isolated from three different mice per genotype. *P<0.05; *P<0.0001. FIGS. 6F: Western blots from sciatic nerves of ten-month-old mice expressing HSPB1$^{WT}$ or mutant HSPB1 probed with antibodies to acetylated tubulin. Equal loading was confirmed by staining for α-tubulin. n=3. FIGS. 6G and 6H: Quantification of the optical densities of acetylated tubulin bands on Western blots of sciatic nerve (FIG. 6G) and spinal cord (FIG. 6H) extracts. Signals are normalized to total α-tubulin levels. n=3. FIG. 6I: Acetylated α-tubulin in sciatic nerve and spinal cord of ten-month-old transgenic mice, as determined by ELISA. Signals are normalized to total α-tubulin levels. n=3. One-way ANOVA. *P<0.0001. Statistical analysis of FIGS. 6B, 6C, 6G and 6H was done with one-way ANOVA. Statistical analysis of FIGS. 6D and 6E was done with Student's t test. Statistical analysis of FIG. 6I was done with Fisher's exact test. Data are presented as means±s.e.m.

FIGS. 8A-8I: HDAC6 inhibition rescues axonal transport defects and restores the CMT2 phenotype. FIGS. 8A and 8B: Axonal transport of mitochondria measured in DRG neurons isolated from ten-month-old HSPB1$^{S135F}$-expressing mice after 12 hours of treatment with TSA (0.4 μM), tubacin (2 μM), tubastatin A (1 μM) or an equivalent amount of DMSO. Total number of (FIG. 8A) and number of moving (FIG. 8B) mitochondria (per 200 seconds and per 100 μm) were quantified. n=20 to 30 cells isolated from three different mice for each condition. *P<0.05; P<0.01; *P<0.0001. FIGS. 8C and 8D: Western blots of sciatic nerve and spinal cord extracts from symptomatic eight-month-old HSPB1$^{S135F}$-expressing mice treated daily for three weeks with TSA (10 mg per kg body weight; FIG. 8C) or tubastatin A (25 mg per kg body weight; FIG. 8D) probed against acetylated tubulin. Equal loading was confirmed with α-tubulin staining. n=3. FIGS. 8E and 8F: Quantifications of optical density (OD) of acetylated tubulin on Western blots of sciatic nerve (FIG. 8E) and spinal cord (FIG. 8F) extracts of symptomatic HSPB1$^{S135F}$-expressing mice treated with TSA or tubastatin A. n=3. FIG. 8G: Motor performance on an accelerating rotarod of HSPB1$^{S135F}$-expressing mice treated for three weeks with TSA or tubastatin A. FIGS. 8H and 8I: Effect of the TSA or tubastatin A treatments of HSPB1$^{S135F}$-expressing mice on the amplitudes of CMAPs (FIG. 8H) or SNAPs (FIG. 8I). n=3 to 6 mice per group. *P<0.05; P<0.001; *P<0.0001. One-way ANOVA was used to analyze the data in FIGS. 8A, 8B, and 8E through 8I. Data are presented as means±s.e.m.

DETAILED DESCRIPTION

Definitions

Figure 1A:
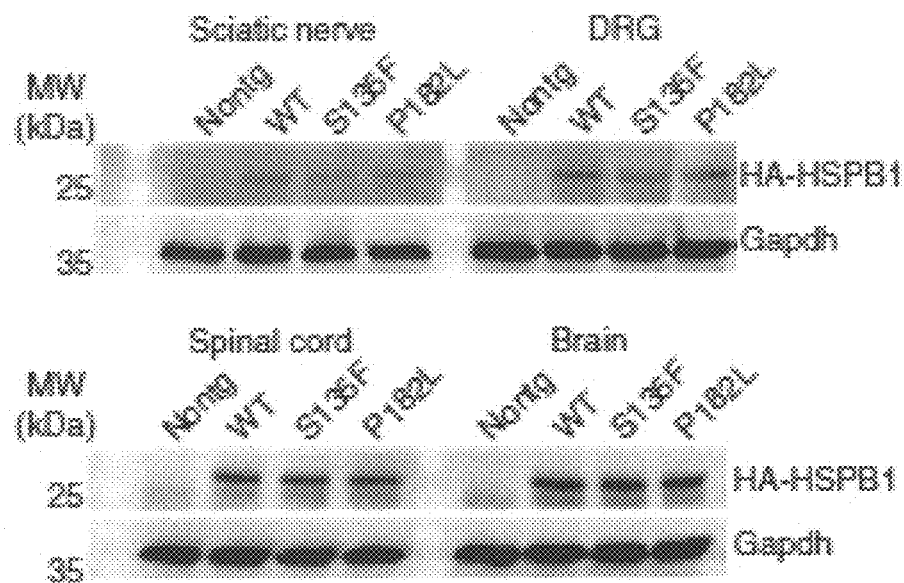
FIGS. 1A-1E: Neuronal expression of human mutant HSPB1 in mice leads to progressive motor defects and decreased muscle strength.

The disclosure will be described with respect to particular embodiments and with reference to certain drawings, but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the description and claims, it does not exclude other elements or steps. Where an indefinite or definite article is used when referring to a singular noun, e.g., "an," or "the," this includes a plural of that noun unless something else is specifically stated.

Furthermore, the terms "first," "second," "third," and the like in the description and in the claims, are used for distinguishing between similar elements and not necessarily for describing a sequential or chronological order. It is to be understood that the terms so used are interchangeable under appropriate circumstances and that the embodiments described herein are capable of operation in other sequences than described or illustrated herein.

The following terms or definitions are provided solely to aid in the understanding of the disclosure. Unless specifically defined herein, all terms used herein have the same meaning as they would to one skilled in the art hereof. Practitioners are particularly directed to Sambrook et al., *Molecular Cloning: A Laboratory Manual*, $2^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

The terms "HDAC" or "HDACs" as used herein refer to histone deacetylases, enzymes responsible for reversible protein deacetylation (EC number 3.5.1). To date, eighteen HDAC family members have been identified. They can be divided into two categories, i.e., zinc-dependent enzymes (Class I, Class II and Class IV) and nicotinamide adenine dinucleotide-dependent enzymes (Class III: sirtuins). Class I HDACs include HDAC1, HDAC2, HDAC3 and HDAC8 and show homology to the yeast protein-reduced potassium deficiency 3. Class II HDACs include HDAC4, HDAC5, HDAC6, HDAC7, HDAC9 and HDAC10 and are homologous to the yeast enzyme HDA1. Class II HDACs are further grouped into two subclasses, IIa (HDAC4, HDAC5, HDAC7, and HDAC9) and IIb (HDAC6 and HDAC10), according to their sequence homology and domain organization. HDAC11, the most recently identified member, is classified into the new Class IV of HDACs. Sirtuins, including human sirtuin (SIRT) 1-7 show distinct homology with the yeast enzyme Sir2.

The term "HDAC inhibitor" is used herein to refer to a molecule capable of inhibiting the deacetylase function of one or more HDACs. HDAC inhibitors are well known in the art and include, but are not limited to, trifluoroacetylthiophene-carboxamides, tubacin, tubastatin A, WT 161, PCI-34051, MC1568, MC1575, suberoylanilide hydroxamic acid (also known as vorinostat or SAHA), Trichostatin A, sodium butyrate, valproic acid, M344, Sriptaid, Trapoxin, Depsipeptide (also known as Romidepsin), MS275 (Entinostat), 4-phenylimidazole, MC1293, droxinostat, curcumin, belinostat (PXD101), panobinostat (LBH589), MGCD0103 (mocetinostat), parthenolide and givinostat (ITF2357).

A "selective HDAC inhibitor" or "specific HDAC inhibitor" is an inhibitor that selectively inhibits certain HDACs, while it does not inhibit others, or inhibits others to a much lower extent. For instance, a selective HDAC6 inhibitor will inhibit HDAC6, but not other HDACs; or it will be more active toward HDAC6. A selective class II HDAC inhibitor will typically inhibit class II HDACs, but not class I HDACs (or only to a much lower extent).

Particularly, a selective HDAC inhibitor will be two times more active toward the targeted HDAC(s) than to those non targeted, or four times more active, or six times more active, or eight times more active, or ten times more active, or 20 times more active, or even 50 times more active, or more. Examples of selective HDAC6 inhibitors include, but are not limited to, tubacin, tubastatin A, WT161, pyridylalanine-containing hydroxamic acids (Schafer et al., *Chem. Med. Chem.* 2009; 4(2):283-90), C3 ethyl-substituted SAHA (Choi et al., *Bioorg. Med. Chem. Lett.* 2011; 21(20):6139-42). WO2011/091213 describes reverse amide compounds that are also selective HDAC6 inhibitors; their use is also explicitly envisaged. The scriptaid isosteres described in WO2010/086646, particularly the amide compounds in Examples 1-15 of that application (i.e., N-Hydroxy-7,7-di(pyridin-2-yl)hept-6-enamide, 6-(Dipyridin-2-ylamino)-N-hydroxyhexanamide, 7-(Dipyridin-2-ylamino)-N-hydroxyheptanamide, N-Hydroxy-7-(pyridin-2-yl(quinolin-2-yl)amino)heptanamide, N-Hydroxy-8,8-di(pyridin-2-yl)oct-7-enamide, N-Hydroxy-7-((4-methylpyridin-2-yl) (pyridin-2-yl)amino)heptanamide, N-Hydroxy-7-((4-phenylpyridin-2-yl)(pyridin-2-yl) amino)heptanamide, N-Hydroxy-7-((5-methylpyridin-2-yl) (pyridin-2-yl)amino)heptanamide, 7-((5-(Benzyloxy) pyridin-2-yl)(pyridin-2-yl)amino)-N-hydroxyheptanamide, N-Hydroxy-7-((5-methoxypyridin-2-yl)(pyridin-2-yl) amino)heptanamide, N-Hydroxy-7-((5-phenylpyridin-2-yl) (pyridin-2-yl)amino)heptanamide, 74(5-(4-Fluorophenyl) pyridin-2-yl)(pyridin-2-yl)amino)-N-hydroxyheptanamide, 7-(lsoquinolin-3-yl-pyridin-2-yl-amino)-heptanoic acid hydroxyamide, 7-[(4-Benzyloxy-pyridin-2-yl)-pyridin-2-yl-amino]-heptanoic acid hydroxyamide), are also HDAC inhibitors with particular selectivity for HDAC6 and thus explicitly envisaged.

Examples of selective type II HDAC inhibitors include, but are not limited to, MC1568 and MC1575. Droxinostat is an example of an inhibitor selective for HDAC3, 6 and 8. Bufexamac is an inhibitor selective for type IIb HDACs, i.e., HDAC6 and HDAC10 (Bantscheff et al., *Nature Biotechnology* 29, 255-265 (2011)). Examples of non-selective HDAC inhibitors include, but are not limited to, trichostatin A, SAHA and valproic acid. Depsipeptides that inhibit HDACs, but of which no selectivity is disclosed, are reported in WO2008/062201, WO2009/022182, WO2009/141657, WO/2009/141658, WO2009/141659, and WO2010/116173.

Described is the use of HDAC inhibitors to treat a peripheral neuropathy, particularly Charcot-Marie-Tooth disease (CMT). Or, equivalently, described are methods of treating a peripheral neuropathy, such as Charcot-Marie-Tooth disease, by administering a HDAC inhibitor to the subject who has the neuropathy (particularly Charcot-Marie-Tooth disease). These wordings are considered equivalent, but comply with the different requirements with patentability across jurisdictions. It is to be understood that embodiments envisaged for methods of treatment also apply for the use of a compound to treat the disease and vice versa.

The findings herein are applicable to numerous neuropathies, as they address a fundamental underlying principle, rather than specific symptoms associated with a particular disease. That is, it is shown that restoring of muscle reinnervation is possible, through recreation of new neuromuscular junctions. Thus, any disease or disorder in which loss of neuromuscular junctions is one of the symptoms can, in principle, be treated in this way. This particularly applies to diseases that have this as a major phenotype, such as peripheral neuropathies (that don't have a central component), either hereditary (e.g., CMT) or induced (e.g., chemotherapy-induced peripheral neuropathy).

Although all types of peripheral neuropathy will benefit, at least to some degree, from the treatment as described herein, most beneficial effects are to be expected when the disorder is an axonopathy, i.e., when axons are primarily affected. This is because the HDAC inhibition as proposed herein has direct effects on axonal transport, and not on the myelin sheaths. Thus, in myelinopathies (where the myelin is first affected and the axons are secondarily affected), an improvement of symptoms is also expected (because of the secondary involvement of axons), but not always a complete recovery. However, it should be stressed that complete recovery is possible for myelinopathies as well, although this might require a chronic treatment to sustain protection of the unsheathed axons.

Thus, also for treatment of Charcot-Marie-Tooth, it is primarily envisaged to treat CMT with an axonal component—recovery in CMT2 or distal HMN is expected to be more complete, although CMT1 (the demyelinating form) is envisaged as well for treatment of symptoms.

A most particularly envisaged subclass of CMT2 or distal HMN are the diseases caused by mutations in HSPB1 (entry 602195 in OMIM). The exact pathogenic mechanism by which mutations in HSPB1 cause CMT2F and/or distal HMN2B is unknown. In vitro, mutant HSPB1 formed intracellular aggregates and inhibited cell division and/or caused neuronal death.[3,12,13] Moreover, mutant HSPB1 disrupted the neurofilament network, thereby disturbing the intracellular distribution of specific cargoes.[12,13] In order to elucidate the pathological mechanisms underlying CMT2 and/or distal HMN, we developed and characterized transgenic mouse models for mutant HSPB1-induced CMT2 and distal HMN. We found that mice expressing mutant HSPB1 selectively in neurons recapitulate all key features of CMT2 or distal HMN, depending on the mutation. Evidence is provided that mutant HSPB1 leads to severe axonal transport defects in a cell-autonomous way. The clinical phenotype of the mutant HSPB1 mice and the axonal transport defects caused by mutant HSPB1 can be rescued by inhibition of histone deacetylase 6 (HDAC6), indicating that HDAC6 plays a crucial role in the pathology of mutant HSPB1-induced peripheral neuropathies.

The data shows that the neuronal expression of human HSPB1 with the S135F mutation results in a CMT2 phenotype, while the P182L mutation leads to a distal HMN phenotype in mice. These two animal models recapitulate the key features of these two diseases and closely resemble human clinical symptoms. Using these newly created mouse models, we discovered that the phenotypes are characterized by disturbances of mitochondrial motility within the axons, which is accompanied by a decrease of acetylated α-tubulin levels. Pharmacological inhibition of HDAC6 rescues the CMT2 phenotype in mutant HSPB1 mice and restores the axonal transport defect in neurons.

HSPB1$^{S135F}$ and HSPB1$^{P182L}$ mice develop an adult-onset, slowly progressing disease without an effect on survival. This is reminiscent of what is observed in CMT2 and distal HMN diseases that start in adulthood, progress slowly and have no major impact on the lifespan of the patients.[3,8-11] Both mutant HSPB1 lines also demonstrate several other key features of these axonal neuropathies. Axonal degeneration appears to be involved in a length-dependent way. Both mutant HSPB1 lines also show signs of distal axonal loss in motor nerve fibers upon electrophysiological assessment. No signs of demyelination of the motor nerve fibers were observed. The reduced CMAP amplitudes but unaffected motor nerve latencies are in agreement with the observations in CMT2 and distal HMN patients.[3,8-11] Histological examination of the mutant HSPB1 gastrocnemius muscle demonstrate neurogenic pathological signs such as pyknotic nuclear clumps and atrophic type 2 muscle fibers and type 1 fiber grouping, all hallmarks of axonal loss. The dramatic reduction in motor axons in peripheral nerves and the decrease in innervated neuromuscular junctions in the gastrocnemius muscle further confirm the motor neuropathy in mutant HSPB1 mice. The altered gait pattern as shown by a pronounced increase in paw angle of the hind paws and shortened step cycles are indicative for a steppage gait. In addition, symptomatic mutant HSPB1 mice have clawed hind paws. All these phenotypic characteristics accurately mimic what is seen in CMT2 and distal HMN. These patients show distal limb muscle weakening and atrophy as well as reduced or absent deep tendon reflexes leading to foot deformities (such as pes cavus and hammertoes) and steppage gait.[3, 8-11]

A striking difference between the two mutant HSPB1 mice is the relative severity of the motor phenotype. HSPB1$^{P182L}$ mice show an earlier reduction in general motor coordination and in muscle force compared to HSPB1$^{S135F}$ mice. Furthermore, the reduction in both motor coordination and muscle force, as well as the disturbance in the hind paw angle, is always more pronounced in HSPB1$^{P182L}$ mice than in the HSPB1$^{S135F}$ mice. The severity of the motor phenotype in HSPB1$^{P182L}$ mice is also reflected in the electrophysiological findings. HSPB1$^{P182L}$ mice have a more pronounced age-dependent reduction in CMAP amplitudes compared to HSPB1$^{S135F}$ mice. These findings are in agreement with the more severe clinical symptoms in patients with the P182L mutation compared to patients with other HSPB1 mutations.[26]

Another difference between both mouse models is the involvement of the sensory system. The HSPB1$^{S135F}$ mice have a mixed sensorimotor polyneuropathy, while the HSPB1$^{P182L}$ mice have a pure motor neuropathy. This is indicated by the observation that HSPB1$^{S135F}$ mice show prolonged response latencies to increased temperature, while the HSPB1$^{P182L}$ mice did not. Electrophysiological findings confirm this difference as only the HSPB1$^{S135F}$ mice have reduced SNAP amplitudes. Furthermore, loss of small sensory axons was observed in HSPB1$^{S135F}$ mice, while these sensory axons were spared in HSPB1$^{P182L}$ mice. This phenotypic distinction was also confirmed in vitro, as DRG neurons isolated from symptomatic HSPB1$^{P182L}$ did not show any abnormalities in axonal transport of mitochondria. Altogether, this situation mimics perfectly the human condition as patients carrying the S135F mutation can have a sensorimotor polyneuropathy, while patients with the P182L mutation have a pure motor neuropathy.[1,3,4,8-11] These data argue against the hypothesis that HSPB1 mutations inducing a sensorimotor phenotype are more severe than mutations inducing a motor phenotype only. Thus, the selectivity of involvement has a qualitative rather than a quantitative aspect to it. Research into the selectivity issue is seriously hampered by the use of the Thy1.2 expression cassette that selectively drives the expression of the transgene in postnatal neurons and that motor neurons can only be cultured from embryos. Moreover, cultured DRG neurons only show a phenotype when isolated from symptomatic animals and thus indicates that only studying neurons from sick animals is useful. The fact that both mutations are situated in different domains of the HSPB1 proteins seems to imply that different cell types show a different sensitivity to the negative effects of these mutated proteins. With respect to this, it is interesting to note that, in patients, mutations situated in the C-terminal part of the protein mainly affect motor axons, while mutations in the N-terminal region and in the α-crystallin domain are affecting in general both motor and sensory neurons.

Furthermore, the results indicate that mutant HSPB1 can cause the phenotypes in a cell-autonomous way as expression of human HSPB1 is limited to neurons in the transgenic mice and this is sufficient to induce the CMT2 or distal HMN phenotypes. The cell-autonomous pathology of mutant HSPB1-induced CMT2 and distal HMN is in line with findings in other CMT2 models. Neuron-specific expression in mutant mitofusin 2 (MFN2) mice showed reduced mass of anterior hind limb muscles, ultimately resulting in limp hind paws.[27] Another mouse model with neuronal expression of mutant MFN2 showed locomotor impairment and gait defects.[28] Using a tetracycline-responsive gene system, Dequen et al. (2010) recently demonstrated that the selective expression of mutant neurofilament light-chain (NEFL; causing CMT2E) in the nervous system leads to the key features of axonal CMT, including anomalous hind limb posture and loss of muscle innervation.[29]

The phenotypes in our transgenic mice are probably caused by a gain-of-function mechanism. This is in line with the dominant inheritance patterns of mutant HSPB1-induced CMT2 and distal HMN in humans. Furthermore, Hspb1-knockout mice are viable and do not show any overt phenotype (Huang et al., Genesis 2007; 45(8):487-501). These transgenic HSPB1 mouse models provide us the unique opportunity to study the pathological mechanism responsible for the observed phenotypes. As it was previously shown that the presence of HSPB1$^{P182L}$ disturbed the intracellular distribution of specific proteins and organelles in transfected cortical neurons, we first concentrated on axonal transport.[12] Moreover, axonal transport appears to play a crucial role in many neurodegenerative diseases.[30] Although no differences in axonal transport were found in cultured DRG neurons isolated from HSPB1$^{S135F}$ mice before disease onset, mitochondrial transport was severely affected in DRG neurons isolated from symptomatic mutant HSPB1$^{S135F}$ mice. This seems to be a common theme in CMT as alterations in mitochondrial transport were also observed in other CMT2 models. Mutations in mitochondrial proteins such as MFN2 (causing CMT2A) and ganglioside-induced differentiation-associated protein 1 (GDAP1, causing CMT2K) affected mitochondrial motility in transfected cell lines.[31-33] Mutant MFN2 showed an increased tethering to the endoplasmic reticulum, which impaired axonal transport of mitochondria in transfected DRG neurons.[31,32] Mutant GDAP1 also affected mitochondrial dynamics partially excluding mitochondria from axons.[33] Mutant NEFL also led to mitochondrial dysfunction prior to neurofilament network disruption.[34] Furthermore, other proteins involved in axonal transport are mutated in patients with CMT2 and/or distal HMN, including the small GTPase RAB7 (CMT2B), emphasizing the central role of axonal transport defects in CMT2 pathology.[2]

Intracellular transport, in particular, along extended processes such as axons, requires motor proteins that distribute their cargoes using guidance cues.[16,35,36] Acetylated α-tubulin is one of these cues.[17,35,36] This is especially true for mitochondrial transport, since moving mitochondria preferentially localize to acetylated microtubules.[35] Moreover, it was shown that disturbance of α-tubulin acetylation plays a role in neurodegenerative diseases such as familial dysautonomia and that increasing acetylated α-tubulin induces an increase in axonal transport.[19,20] We found that total acetylated α-tubulin levels were dramatically decreased in peripheral nerve from mutant HSPB1 mice compared to HSPB1$^{WT}$ animals. This reduction of α-tubulin acetylation is a peripheral (distal) phenomenon, as acetylated α-tubulin levels were not affected in the spinal cord of mutant HSPB1 mice. The cause of this decrease is uncertain. Restoring levels of acetylated α-tubulin by inhibiting HDAC6 (e.g., using TSA, tubacin or tubastatin A) rescued the axonal transport defects suggesting a key role for deacetylation in the mechanism of mutant HSPB1-induced CMT, as it has been shown in other neurodegenerative disorders including Huntington's disease, multiple sclerosis but also peripheral nerve injuries.[37-39] Pharmacological inhibition of HDAC6 also increased mitochondrial transport in hippocampal neurons indicating that HDAC6 regulates axonal transport.[19] TSA and tubastatin A treatment of mutant HSPB1 mice (see Example 9) also partially restored the CMT2 phenotype both at the behavioral and electrophysiological levels, further indicating that reduced acetylated α-tubulin levels play an important role in mutant HSPB1-induced CMT2 pathology.

In se, the effect of TSA could be broader than its effect on mitochondrial transport as it was shown before that treatment with TSA restored the impaired vesicular transport and stimulated the release of essential growth factors, such as brain-derived neurotrophic factor (BDNF), in a mouse model of the Huntington's disease.[40] Moreover, TSA also has an important effect on histone acetylation, thereby influencing gene expression.[25,41,42] In a mouse model for spinal muscular atrophy (SMA), an autosomal recessive motor neuron disease affecting children caused by insufficient SMN, treatment with TSA increased the SMN protein expression leading to an improvement of motor performance and an increase in survival.[25] Besides the importance of histone and tubulin acetylation, it has been shown that lysine acetylation of many other proteins (known as the "acetylome") in general might co-regulate major cellular functions including chromatin remodeling, cell cycle, splicing, nuclear transport and actin nucleation.[43] However, since the same effects were observed using tubacin and tubastatin A, both selective HDAC6 inhibitors, it appears that specific HDAC6 inhibition can recapitulate the effects of pan-HDAC inhibition seen with TSA.

Thus, envisaged is that the HDAC inhibition that is described herein to treat peripheral neuropathy is particular inhibition of type II HDACs (i.e., using a type II HDAC inhibitor), more particularly of type IIb HDACs. According to specific embodiments, the HDAC inhibitor is a selective inhibitor of type II HDACs.

According to most particular embodiments, the HDAC inhibitor is a HDAC6 inhibitor. Even more particularly, the HDAC6 inhibitor is a selective HDAC6 inhibitor. A non-exhaustive list of HDAC and HDAC6 inhibitors that can be used is given above. According to specific embodiments, the HDAC inhibitor is a selective HDAC6 inhibitor selected from tubacin and tubastatin A.

The results presented herein indicate that the phenotype of inherited peripheral neuropathies can be stopped and even reversed by pharmacological inhibition of deacetylation, at least in animal models. Such reversibility was also demonstrated by conditional mutant NEFL mice with CMT2 symptoms, a phenotype that could be restored by switching off the expression of mutant NEFL in symptomatic mice.[29] Most remarkable in this regard is that restoration of acetylated α-tubulin levels through inhibition of HDACs, particularly HDAC6, rescues and reverses the motor performance phenotype as seen in CMT. Indeed, since this phenotype is due to axonal loss and muscle denervation, it can only be rescued by reinnervation of the muscle. This is exactly what is seen in preliminary experiments: lost contacts between nerves and muscles (neuromuscular junctions) are restored, thereby reversing the phenotype. To our knowledge, this is the first time that it is shown that loss of neuromuscular junctions found in neurodegenerative disease can be reversed by a pharmacological treatment. Moreover, the new neuromuscular junctions are functional, thereby allowing rescue of the neurodegenerative phenotype. Without being bound to a particular mechanism, this effect is likely due to the increase in acetylated α-tubulin, as this is important for mitochondrial transport and axonal transport. This mechanism also indicates that the finding of regeneration of functional neuromuscular junctions can be extended to diseases other than CMT, such as all neurodegenerative diseases where axonal transport mediated by microtubuli is important (e.g., Parkinson's, Huntington, MS, spinal muscular atrophy, amyotrophic lateral sclerosis, and Guillain-Barré syndrome; see also references 37-39). Most particularly envisaged, however, are axonopathies (i.e., disorders that are primarily characterized by dysfunctional axons, as opposed to demyelinating diseases, where the myelin sheath covering the axons is first affected). Particularly envisaged are peripheral neuropathies. Of particular note are neuropathies (or axonopathies) induced by external substances, such as drugs. Examples of these include chemotherapy-induced peripheral neuropathy (CIPN) such as, for instance, induced by vinka alkaloids (e.g., vincristine, vinblastine, vindesine and vinorelbine), platinum salts (e.g., cisplatin, oxaliplatin), taxanes (e.g., paclitaxel, docetaxel), epothilones (ixabepilone and others), bortezomib, thalidomide and derivatives. These neuropathies are reviewed in, e.g., Cavaletti et al., *Nat. Rev. Neurol.* 2010, 6(12):657-66, and Balayssac et al., *Expert Opin. Drug. Saf* 2011, 10(3):407-17.

In conclusion, transgenic animals expressing human mutant HSPB1 selectively in neurons has been developed. These mice demonstrate phenotypes that accurately replicate all key features of human symptoms of CMT2 and distal HMN. Mutant HSPB1 cells autonomously affect axonal transport and decrease acetylated α-tubulin levels. The reduction of acetylated α-tubulin levels is reversed by HDAC6 inhibition, which restores the defects in axonal transport and rescues the CMT2 phenotype behaviorally and electrophysiologically.[47] Evidence is provided for the involvement of cytoskeletal changes in mutant HSPB1-induced CMT2 and distal HMN. Inhibition of HDAC6 may be a new therapeutic approach for both diseases, or for peripheral neuropathies in general.

It is to be understood that although particular embodiments and specific configurations, as well as materials and/or molecules, have been discussed herein for cells and methods hereof, various changes or modifications in falai and detail may be made without departing from the scope and spirit of this disclosure. The following examples are provided to better illustrate particular embodiments and they should not be considered limiting the application.

EXAMPLES

Example 1

Mutant HSPB1 Mice Show Progressive Motor Deficits Propagating from Hind Limbs to Forelimbs Transgenic mice were created using a Thy1.2 expression cassette responsible for postnatal and neuron-specific expression of the transgene. The human wild-type (WT) or mutant (S135F and P182L) HSPB1 cDNA coupled to an N-terminal hemagglutinin (HA)-tag were cloned in this construct and transgenic animals were made using zygote injection. Western blot analysis revealed no human HSPB1 expression in non-neuronal tissues such as heart, liver and kidney (not shown). Brain, spinal cord, DRG and peripheral nerve expressed HA-tagged human HSPB1 (FIG. 1A). No significant differences in expression levels of HSPB1 were observed between the different transgenic mice (not shown).

In transgenic mice, human WT or mutant HSPB1 was present only in the grey matter and in extended processes in the white matter (not shown). At the cellular level, HSPB1 co-localized with the neuronal marker SMI-32 in ventral horn of transgenic mouse spinal cord, but not with glial fibrillary acidic protein (GFAP), confirming that human HSPB1 was exclusively expressed in neurons (not shown). In line with other studies using the Thy1.2 expression cassette, no differences were observed in transgene expression between DRG and motor neurons (not shown).

Figure 1B:
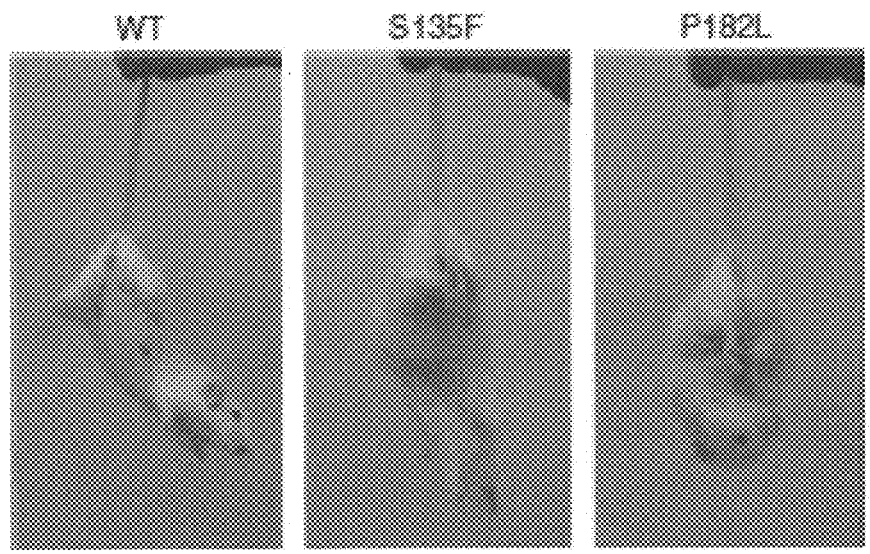
Figure 2:
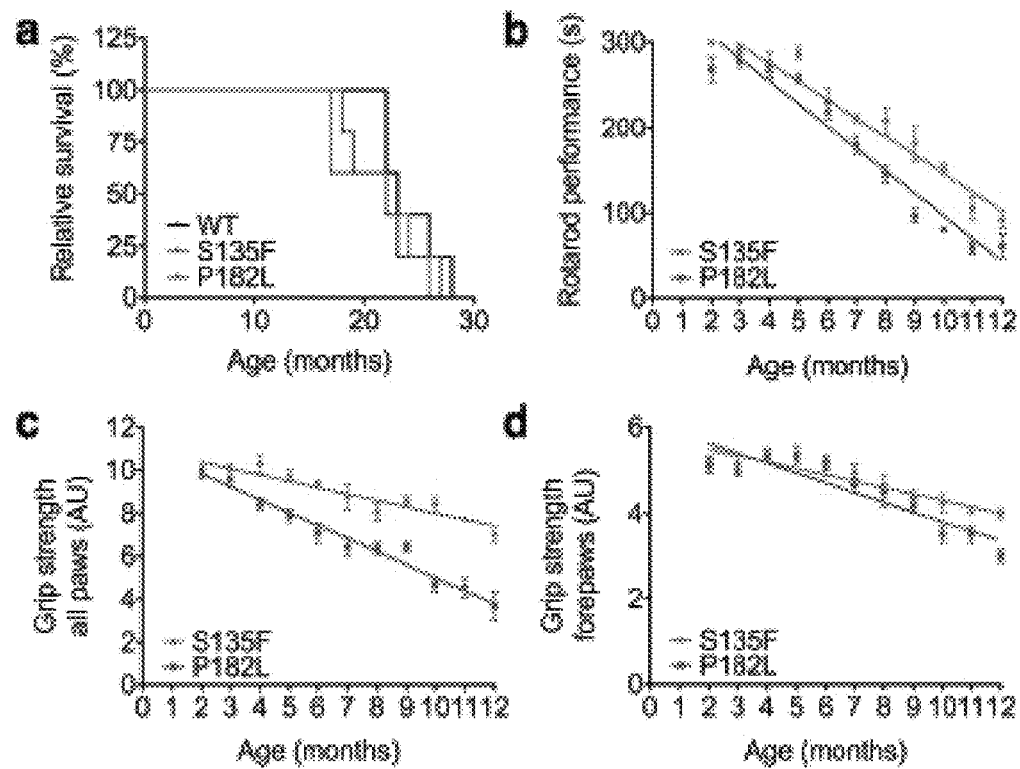
FIG. 2: No effect on survival and more severe motor phenotype in mutant HSPB1$^{P182L}$. Panel a: Kaplan-Meier curve of transgenic WT (black), S135F (red) and P182L (blue) HSPB1 mice. n=5 mice in each group. Log-rank test. P>0.05. Panel b: Linear curve fitting of the averaged data points of the rotarod test over time of both mutant HSPB1 (S135F in red; P182L in blue) mice. Linear regression. $R^2_{S135F}$=0.95; $R^2_{P182L}$=0.94; P=0.02. Panel c: Linear fit of averaged data points of muscle force of all four paws together in function of age for both mutant (S135F in red; P182L in blue) HSPB1 mice. Linear regression. $R^2_{S135F}$=0.86; $R^2_{P182L}$=0.97; P<0.0001. Panel d: Linear fitting of averaged data points over time of muscle force of forepaws only for both mutant (S135F in red; P182L in blue) HSPB1 mice. Linear regression. $R^2_{S135F}$=0.90; $R^2_{P182L}$=0.82; P=0.005.

All transgenic mice were nonoral at birth and showed normal weaning and grooming behavior. The frequency of birth of all transgenic lines followed the normal Mendelian inheritance pattern indicating that there was no embryonic lethality. Furthermore, no differences in survival were observed between all genotypes (P>0.05; FIG. 2, Panel a). However, at six months of age, all mutant (S135F and P182L) HSPB1 mice showed limb-clasping behavior when suspended by the tail, while non-transgenic and HSPB1$^{WT}$ mice never did (FIG. 1B).

Figure 1C:
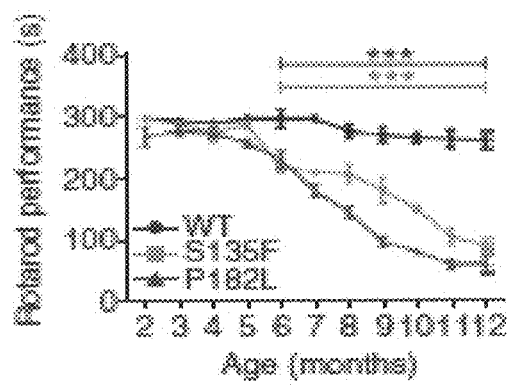

Next, general motor performance was assessed using an accelerating rotarod. All mice could stay on the rotarod (300 seconds) until the age of six months. From that age on, both mutant HSPB1 lines started to fail on the rotarod test and a progressive reduction in performance was observed over time (P<0.0001; FIG. 1C). HSPB1$^{P182L}$-expressing mice showed a more pronounced decline compared to HSPB1$^{S135F}$-expressing mice (FIG. 2, Panel b).

Figure 1D:
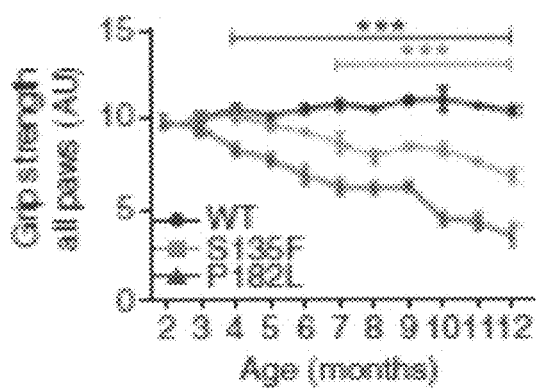
Figure 1E:
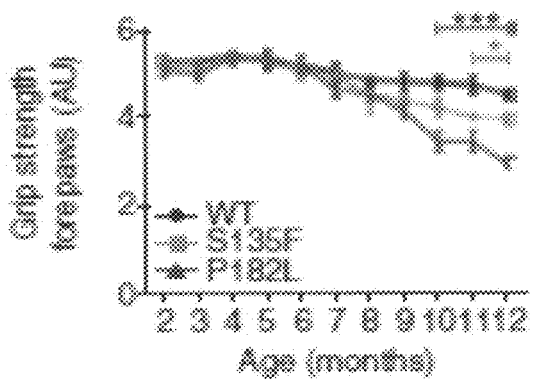

As progressive muscle weakness and atrophy propagating from hind- to forelimbs are important characteristics of CMT2 and distal HMN, the grip strength of the HSPB1 transgenic mice was assessed. A progressive decline in the grip strength of both fore- and hind paws combined for both mutant HSPB1 lines was observed (P<0.0001; FIG. 1D). This decline was more severe for HSPB1$^{P182L}$ than for HSPB1$^{S135F}$ (FIG. 2, Panel c). Grip strength of forepaws only showed a significant decrease from the age of ten months on (P=0.001; FIG. 1E). Again, this decrease was most pronounced for HSPB1$^{P182L}$-expressing mice (FIG. 2, Panel d). All together, these results indicate that both HSPB1$^{S135F}$ and HSPB1$^{P182L}$ mice develop motor deficits progressing from hind limbs to forelimbs and worsening with age.

Example 2

Mutant HSPB1 Mice Demonstrate Steppage Gait

Figure 3:
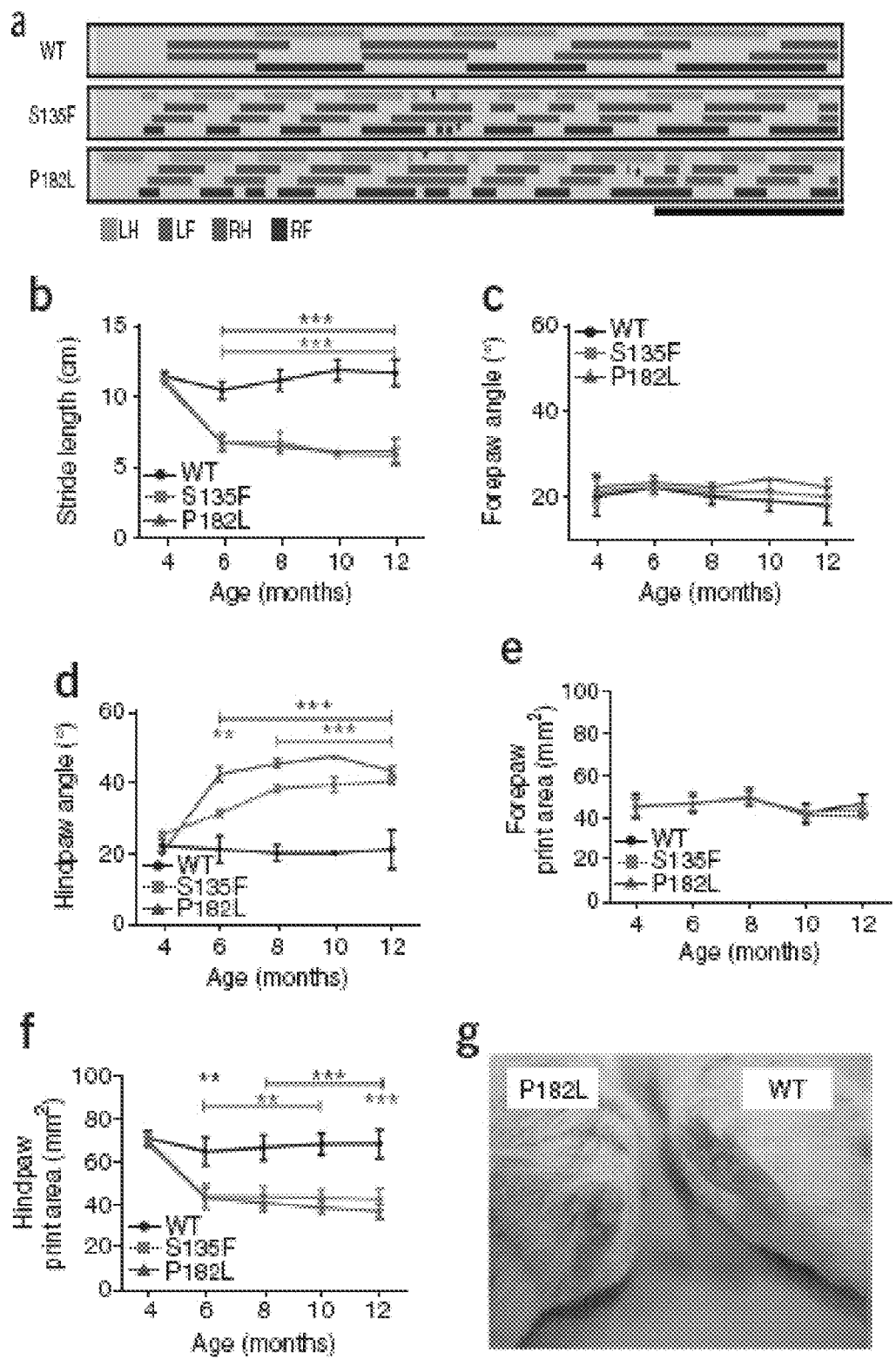
FIG. 3: Mice expressing mutant HSPB1 show steppage gait and clawed hindpaws. Panel a: Typical gait patterns of eight-month-old transgenic mice monitored with the semiautomated Catwalk system. Colored bars represent the time a paw makes contact with the floor plate. LH, left hindpaw; LF, left forepaw; RH, right hindpaw; RF, right forepaw. Asterisks mark hesitations in the gait pattern observed for both mutant HSPB1 mouse lines. Scale bar, 10 cm. Panels b-f: Quantification of various parameters obtained from the gait analysis with the Catwalk. Stride length (Panel b), forepaw angle (Panel c), hind paw angle (Panel d), forepaw print area (Panel e) and hind paw print area (Panel f) were measured as a function of age in mice expressing HSPB1$^{WT}$, HSPB1$^{S135F}$ or HSPB1$^{P182L}$. n=15 mice per genotype. Two-way ANOVA for repeated measures. P<0.001; *P<0.0001. Blue asterisks indicate differences between P182L and WT. Red asterisks indicate differences between S135F and WT. The lines represent the span in which the data points are significantly different. Tukey's HSD test was used for post hoc analysis. Data are presented as means±s.e.m. Panel g: Typical example of a mutant HSPB1$^{P182L}$-expressing mouse showing clawed hind paws.

It was observed that the mutant HSPB1 mice placed their paws in an anomalous manner on the rotating rod. In order to quantify this difference, the gait pattern was monitored using the semi-automated Catwalk™ system as described before.[14,15] From six months on, both mutant HSPB1 lines needed, on average, twice the number of step cycles to cross a 40-cm long walkway compared to HSPB1$^{WT}$ (FIG. 3, Panel a). This resulted in a 50% reduction of the stride length (P<0.0001; FIG. 3, Panel b). Moreover, both mutant HSPB1-expressing mouse lines showed hesitations in placing their paws and had increased hind paw angles and decreased hind paw print areas, whereas forepaws were unaffected (P<0.0001; FIG. 3, Panels a-f). The decrease in hind paw print area is in line with the clawed hind paws observed in mutant HSPB1-expressing mice (FIG. 3, Panel g). These clawed hind paws were more pronounced in mice expressing HSPB1$^{P182L}$ than in those expressing HSPB1$^{S135F}$ and were not observed in mice expressing HSPB1$^{WT}$ or non-transgenic mice. These data clearly demonstrate that mutant HSPB1 mice accurately mimic the steppage gait and foot deformities (such as pes cavus) observed in CMT2 and distal HMN patients.

Example 3

Mutation-Dependent Sensory Deficits in Mutant HSPB1 Mice

Figure 4A:
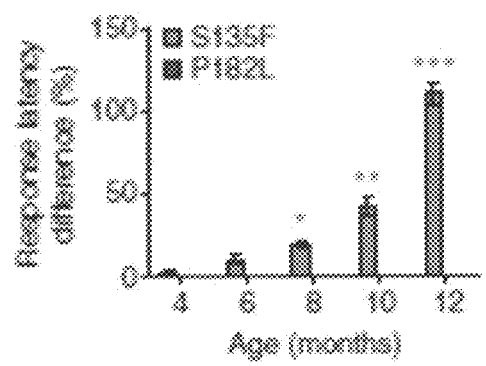

Clinically, the P182L mutation in HSPB1 is associated with a pure motor neuropathy, while patients carrying the S135F mutation can also have sensory deficits, in particular, for pain and temperature.[1,2] Therefore, tests were performed to see whether HSPB1$^{S135F}$ and HSPB1$^{P182L}$ mice showed signs of sensory impairment using the hotplate test. HSPB1$^{S135F}$ mice demonstrated increased response latencies compared to HSPB1$^{WT}$ mice getting more aggravated with age (P=0.01; FIG. 4A). In contrast, HSPB1$^{P182L}$ did not show any differences in response latencies compared to HSPB1$^{WT}$ mice (FIG. 4A), indicating that HSPB1$^{P182L}$ mice have only impaired motor performance while the HSPB1$^{S135F}$ mice have both motor and sensory deficits.

Example 4

Figure 4B:
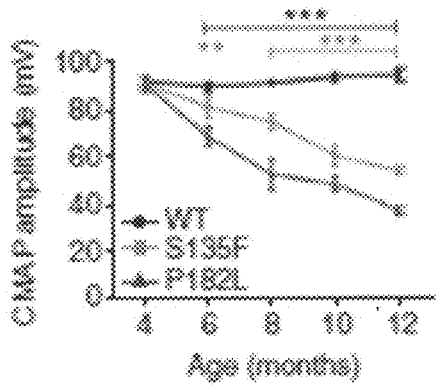
Figure 4C:
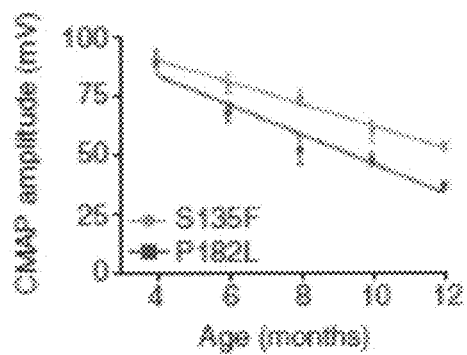
Figure 4D:
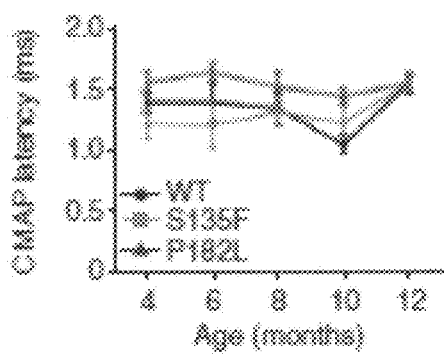
Figure 4E:
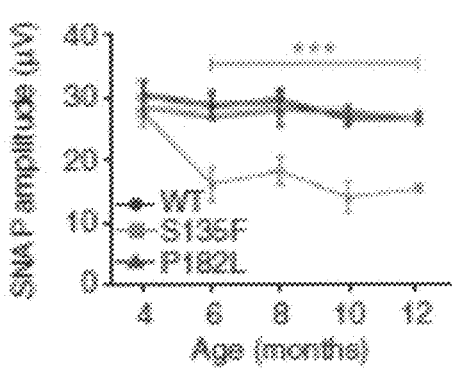
Figure 4F:
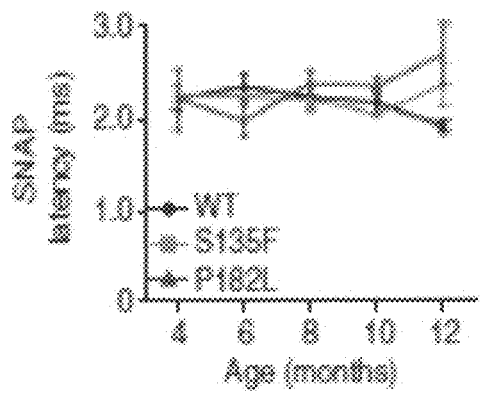

Electrophysiological Studies Reveal Primary Axonal CMT and Distal HMN Phenotypes Nerve conduction studies are routinely done on CMT patients to discriminate demyelinating (type 1) from axonal (type 2) forms, as well as to assess whether patients show either a mixed sensorimotor (CMT2) or a pure motor neuropathy (distal HMN). Therefore, nerve conduction studies were performed on transgenic HSPB1 mice using sub-dermal electrodes, either at the level of the gastrocnemius muscle to measure compound muscle action potentials (CMAPs), or in the distal end of the tail to record sensory nerve action potentials (SNAPs). HSPB1$^{P182L}$ and HSPB1$^{S135F}$ mice showed a significant decrease in peak-to-peak amplitude of CMAPs at six and eight months of age, respectively (P<0.0001; FIG. 4B). The decrease in CMAP amplitudes in function of age was more pronounced in HSPB1$^{P182L}$ compared to HSPB1$^{S135F}$ mice as assessed by the slopes (slope$_{S135F}$=−4.66+0.32; slope$_{P182L}$=−6.23+0.93; P=0.004; FIG. 4C). CMAP latencies were unaffected, confirming the axonal nature of the motor neuropathy in both mutant HSPB1 lines (FIG. 4D). Six-month-old HSPB1$^{S135F}$ mice also showed a significant decrease in baseline-to-peak amplitude of SNAPs, getting more aggravated with age (P<0.0001; FIG. 4E). Again, SNAP latencies were unaltered demonstrating that the sensory loss was due to an axonal neuropathy (FIG. 4F). In contrast, HSPB1$^{P182L}$ mice did not show any reduction in SNAP amplitudes, confirming that this mutant HSPB1 line has no sensory deficits (FIG. 4E).

In HSPB1$^{S135F}$ mice, CMAP amplitudes were significantly decreased compared to HSPB1$^{WT}$ at the age of eight months, while SNAP amplitudes were already significantly lower at the age of six months. Since the recording electrodes for the SNAP amplitudes were placed more distally (4 cm distally from the base of the tail) compared to the electrodes for the CMAP amplitudes (at the level of the gastrocnemius muscle), it was concluded that the axonal neuropathy is length-dependent (i.e., longer axons are affected first). In conclusion, the electrophysiological findings confirm that HSPB1$^{S135F}$ mice have a mixed sensorimotor polyneuropathy (CMT2), while HSPB1$^{P182L}$ mice develop a pure motor neuropathy (distal HMN).

Example 5

Axonal Loss and Muscle Denervation Underlies CMT2 and Distal HMN Phenotypes

Figure 5:
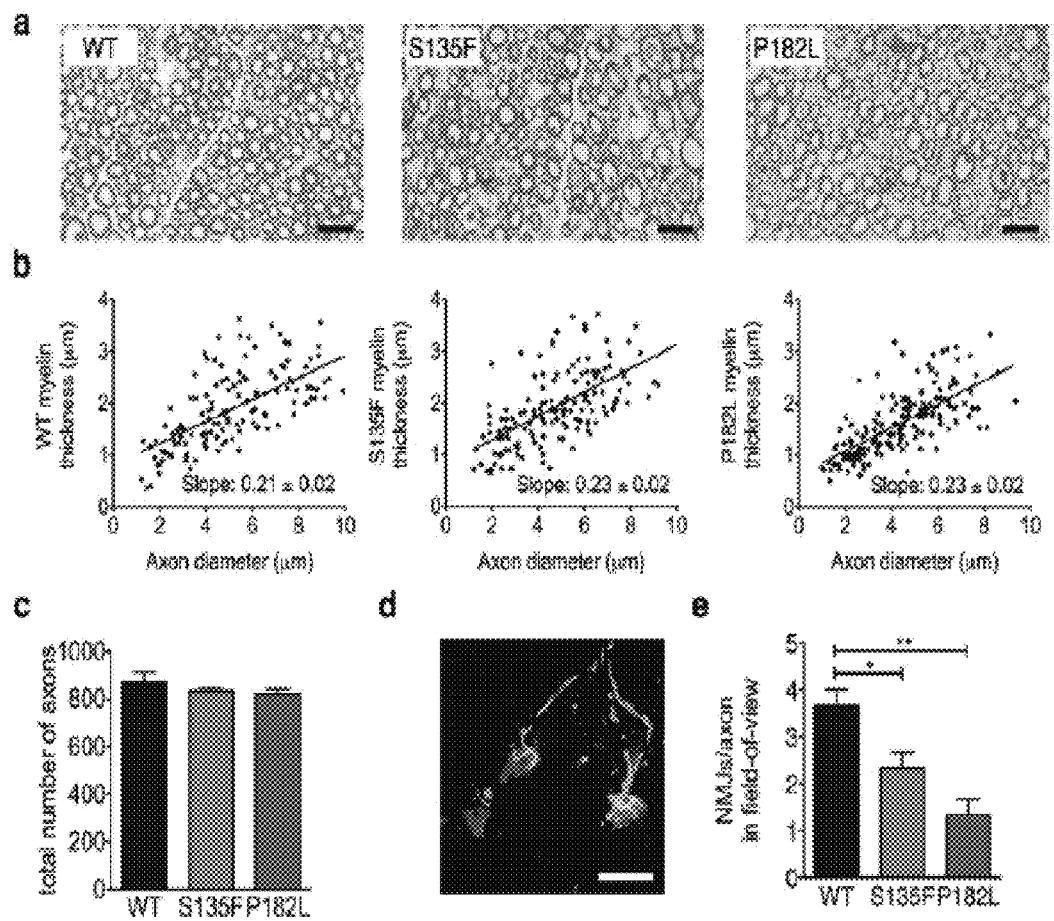
FIG. 5: Mutant HSPB1-induced neuropathy caused no proximal axonal loss, but is characterized by muscle denervation. Panel a: Toluidine blue staining of semi-thin proximal sciatic nerve sections of ten-month-old HSPB1$^{WT}$ (left panel) and mutant HSPB1 (middle and right panel) mice showing no axonal loss. No signs of demyelination were observed. Scale bar 40 μm. Panel b: Correlation of myelin thickness and axonal diameter confirming the absence of demyelination in HSPB1WT (left panel) and mutant HSPB1 (middle and right panel) mice. Panel c: Quantification of the number of axons in proximal parts of the sciatic nerve. One-way ANOVA. P>0.05. Panel d: Fluorescent micrograph of acetylcholine-receptor clusters stained with α-bungarotoxin (in red) and terminal axon branch stained with neurofilament heavy chain (Nf200; in green) from a 25 μm thick longitudinal section of gastrocnemius muscle of a ten-month-old HSPB1$^{S135F}$ animal. Scale bar: 20 μm. Panel e: Quantification of the number of acetylcholine-receptor clusters per terminal axon branch visible within a field of view. One-way ANOVA. *P<0.05; P<0.001; *P<0.0001.

No histological evidence for demyelination was found in either proximal or distal parts of the sciatic nerve (FIGS. 4G, 4H, and FIG. 5, Panels a and b) or axonal loss in the proximal part of the sciatic nerve (P>0.05; FIG. 5, Panel c). In contrast, there was a significant decrease in the number of axons in distal parts of the sciatic nerve in both HSPB1$^{135F}$-expressing and HSPB1$^{P182L}$-expressing mice (P=0.002 and P=0.001, respectively; FIG. 4I).

In the gastrocnemius muscle, less acetylcholine receptor clusters per terminal axon was found in mice expressing mutant HSPB1 compared to HSPB1$^{WT}$-expressing mice (FIG. 5, Panels d and e). HSPB1$^{WT}$-expressing mice had almost no visibly denervated neuromuscular junctions, whereas, of the remaining neuromuscular junctions, HSPB1$^{S135F}$-expressing and HSPB1$^{P182L}$-expressing mice showed a marked increase of denervated neuromuscular junctions (FIG. 4J).

Both mutant HSPB1-expressing mouse lines showed atrophic muscle fibers in the gastrocnemius muscle accompanied by pyknotic nuclear clumps (data not shown). Fiber type grouping was observed in muscles from both mutant HSPB1-expressing mouse lines, whereas muscle fibers showed a normal "checkerboard" appearance in HSPB1$^{WT}$-expressing mice (not shown). Taken together, histological examination of hind limb muscles and peripheral nerves confirms that HSPB1$^{S135F}$ mice have a mixed sensorimotor axonal polyneuropathy (CMT2), while HSPB1$^{P182L}$ mice develop a pure motor axonal neuropathy (distal HMN), which completely mimics human conditions. The defects are not due to demyelination, but to distal axonal loss.

Example 6

HSPB1$^{S135F}$ Causes Axonal Transport Defects

It has previously been shown that the intracellular distribution of specific cargoes, such as mutant HSPB1 itself, but also neurofilament and p150, was disturbed in cortical neurons transfected with HSPB1$^{P182L}$ (ref. 12). In order to study effects of mutant HSPB1 on axonal transport, dorsal root ganglion (DRG) neurons from adult transgenic mice were isolated and analyzed mitochondrial transport in these neurons after two days in culture. Mitochondrial movement was visualized by loading DRG neurons with a selective mitochondrial marker (M$_{ito}$T$_{racker}$®) and by live video imaging (FIG. 6A). Kymographs resulting from time compression of video images were used to quantify the total number of mitochondria present in the neurites and to discriminate antero- and retrogradely moving from stationary mitochondria (FIG. 6A, right-side panels).

DRG neurons isolated from symptomatic HSPB1$^{S135F}$ mice showed a dramatic reduction of the number of moving mitochondria compared to HSPB1$^{WT}$ (P<0.0001; FIGS. 6A and 6B). In addition, significantly less mitochondria were present in their neurites compared to HSPB1$^{WT}$ (P=0.01; FIGS. 6A and 6C). HSPB1$^{P182L}$ DRG neurons did not show any difference in either total number of mitochondria or moving mitochondria, consistent with the pure motor phenotype of these mice (P>0.05; FIGS. 6B and 6C), and mitochondrial transport was also unaffected in DRG neurons isolated from presymptomatic mutant HSPB1$^{S135F}$-expressing mice (FIGS. 6D and 6E). This shows that the disturbance of axonal transport in the isolated DRG neurons coincides with the presence of the sensory deficits in the transgenic mice.

Example 7

Mutant HSPB1 Mice Show Reduced Acetylated α-Tubulin Levels

Mitochondria are mainly transported along microtubules consisting of polymerized tubulin.[16] Tubulin can undergo a variety of post-translational modifications such as tyrosination/detyrosination, glutamylation, glycylation and acetylation/deacetylation.[17] Acetylation/deacetylation of α-tubulin was focused on since this process is needed for intracellular trafficking of a wide range of proteins and organelles because it is considered as a recognition signal for the anchoring of molecular motor.[17-19] In addition, decreased levels of acetylated α-tubulin have been associated with neurodegenerative diseases.[20,21]

In peripheral nerve homogenates of ten-month-old mutant HSPB1 mice, a dramatic decrease in acetylated α-tubulin levels was observed in the presence of mutant HSPB1 compared to HSPB1$^{WT}$ (P<0.0001; FIGS. 6F and 6G). Interestingly, in spinal cord homogenates, no significant differences in acetylated α-tubulin levels were observed (P>0.05; FIGS. 6F and 6H). Using ELISA, the decrease in acetylated α-tubulin levels in sciatic nerve of mutant HSPB1 mice was confirmed (P<0.0001; FIG. 6I). Longitudinal sections of sciatic nerves demonstrated lower levels of acetylated α-tubulin levels in mutant HSPB1 mice compared to HSPB1$^{WT}$ animals (data not shown).

Example 8

HDAC6 Inhibition Rescues Axonal Transport Defects in Cultured HSPB1$^{S135F}$ Neurons Acetylation and deacetylation is unique among the tubulin modifications in that it occurs within the luminal side of microtubules at lysine-40 of α-tubulin.[18] Histone deacetylase 6 (HDAC6), a class II histone deacetylase, is the major enzyme that interacts with α-tubulin and demonstrates α-tubulin deacetylating activity.[22,23] Moreover, it has been shown in cultured hippocampal neurons that HDAC6 can regulate the axonal transport of mitochondria.[19]

Figure 7:
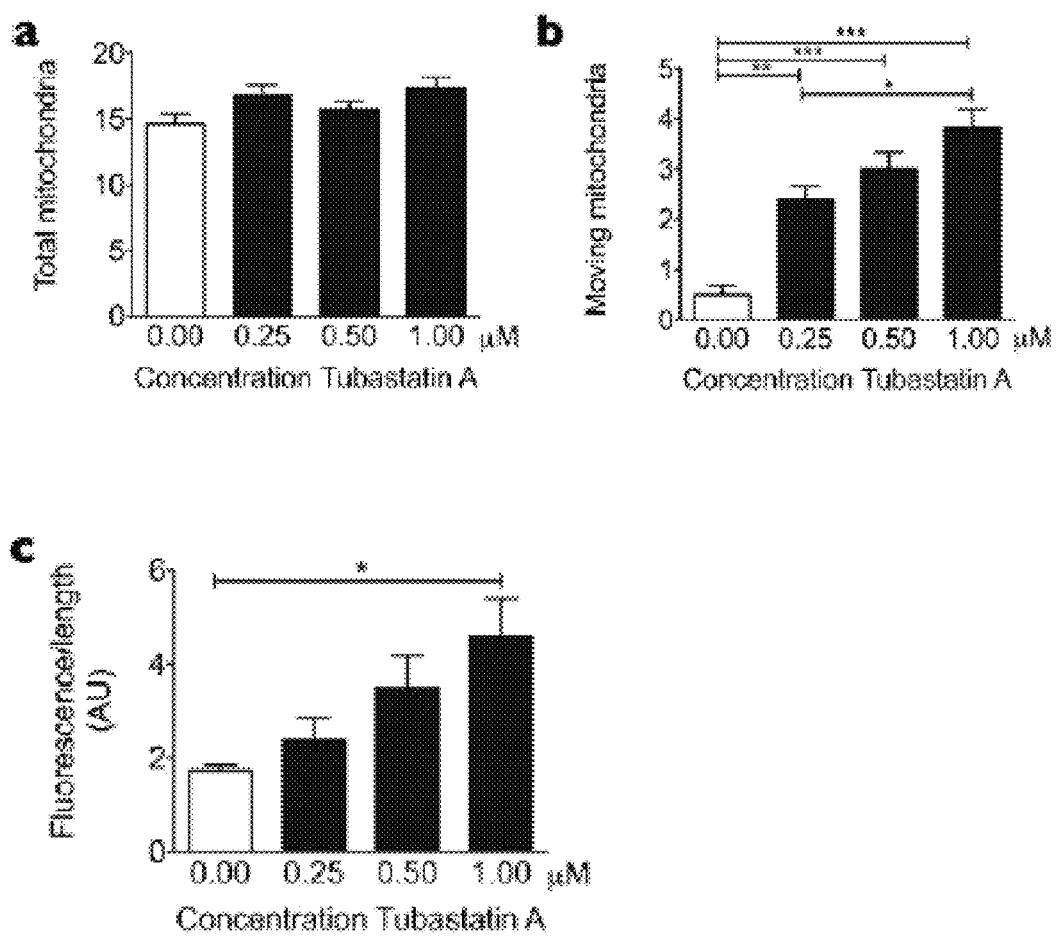
FIG. 7: Tubastatin A dose-dependently rescued axonal transport and increased acetyl-tubulin levels in vitro. Panels a and b: Axonal transport of mitochondria was assessed in DRG neurons isolated from symptomatic (eight-month-old) HSPB1$^{S135F}$ mice after 12 hours incubation with various concentrations (0, 0.25, 0.50 or 1.00 μM) of Tubastatin A. Panel a: Quantification of the total number of mitochondria at various concentrations of Tubastatin A. One-way ANOVA. P>0.05. Panel b: Quantification of the number of moving mitochondria at different concentrations of Tubastatin A. One-way ANOVA. *P<0.05; **P<0.001; P<0.0001. Panel c: Quantification of the integrated density of the acetylated tubulin signal along neurites at various concentrations of Tubastatin A. n=25 to 30 cells/condition. One-way ANOVA. *P<0.05.

To demonstrate a direct link between HDAC6 and the pathological mechanism underlying mutant HSPB1-induced CMT2, DRG neurons were incubated with several HDAC6 inhibitors. Trichostatin A (TSA) is a pan-HDAC inhibitor that selectively inhibits the deacetylating function of class I and class II (but not class III) HDACs, whereas both tubacin and tubastatin A (FIG. 7) are highly selective HDAC6 inhibitors (refs. 24 and 46). Treatment of DRG neurons isolated from symptomatic HSPB1$^{S135F}$-expressing mice with TSA, tubacin or tubastatin A increased total numbers of mitochondria (FIG. 8A) and restored the number of moving mitochondria (FIG. 8B). Tubacin and tubastatin A were more effective compared to TSA (FIGS. 8A and 8B).

Example 9

HDAC6 Inhibition In Vivo Corrects the CMT2 Phenotype in Mutant HSPB1 Mice

Figure 8C:
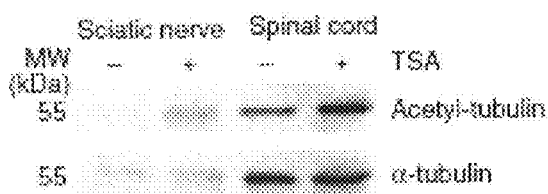
Figure 8D:
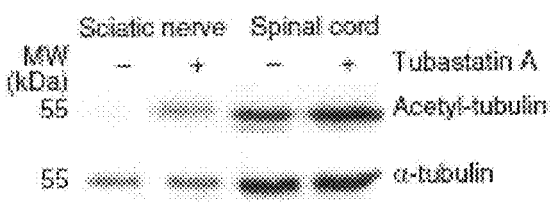

Next, symptomatic HSPB1$^{S135F}$-expressing mice were treated for 21 days with either a nonspecific or a specific HDAC6 inhibitor. TSA and tubastatin A treatment resulted in a significant increase of acetylated α-tubulin amounts in peripheral nerves (P=0.009 and P<0.008, respectively; FIGS. 8C-8E). TSA, but not tubastatin A, also increased acetylated α-tubulin amounts in spinal cord (FIG. 8C, 8D, and 8F). Both TSA and tubastatin A did not affect overall α-tubulin abundance (FIGS. 8C and 8D).

Figure 8I:
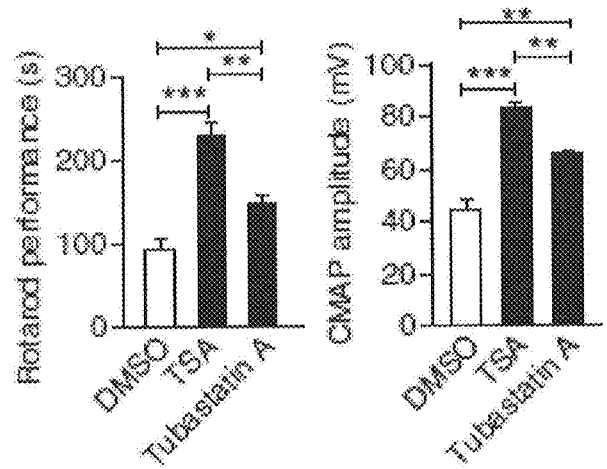
Figure 8I:
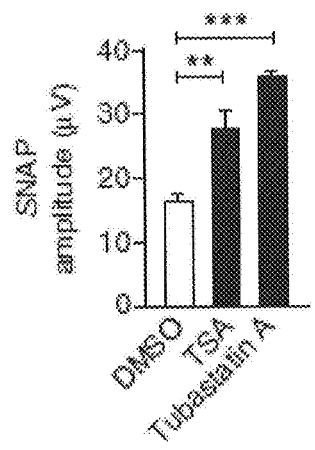
Figure 9:
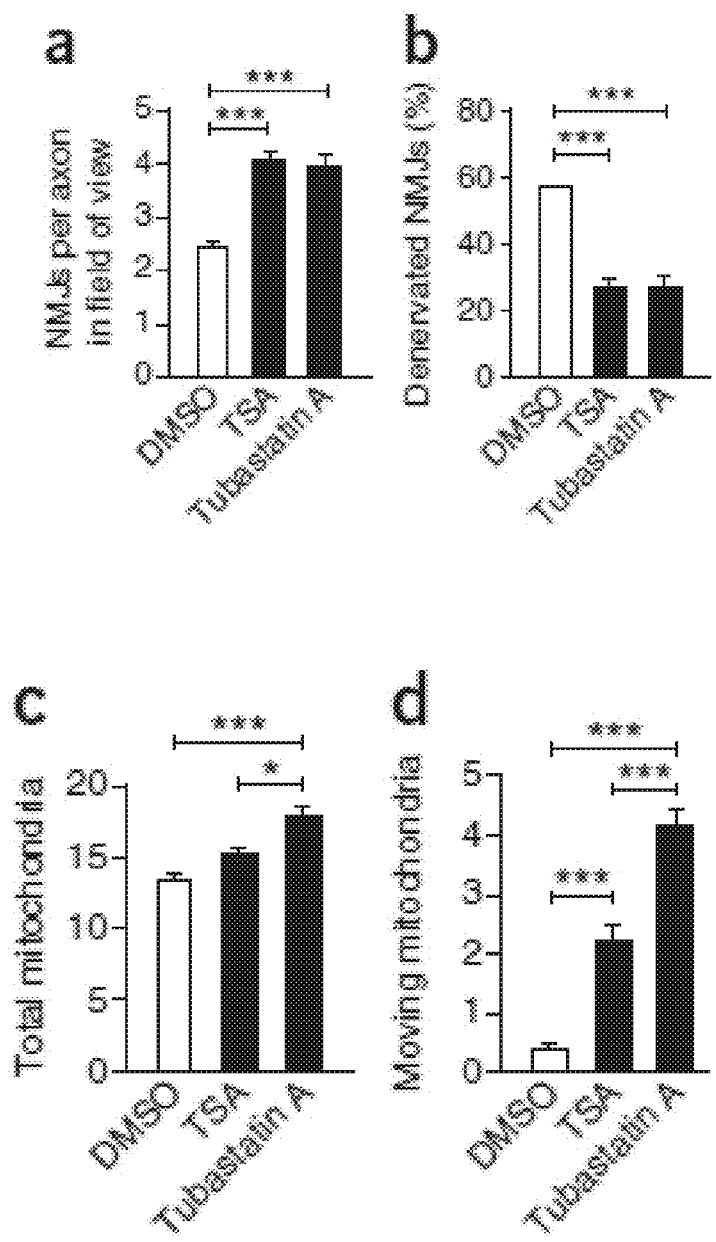
FIG. 9: TSA or tubastatin A treatment leads to muscle reinnervation and rescues axonal transport defects. Panels a and b: Effect of vehicle (DMSO), TSA or tubastatin A treatment on the innervation level of the gastrocnemius muscle in symptomatic, eight-month-old HSPB1$^{S135F}$-expressing mice. The number of visible neuromuscular junctions (NMJs) per axon in each field of view (Panel a) and the relative quantity of denervated neuromuscular junctions (Panel b) were determined after staining gastrocnemius muscle with antibodies against α-bungarotoxin and neurofilament heavy chain. n=2 or 3 mice per condition. ***P<0.0001. Panels c and d: Axonal transport of mitochondria measured in cultured DRG neurons isolated from symptomatic HSPB1$^{S135F}$-expressing mice after three weeks of treatment with TSA or tubastatin A. Total number (Panel c) and number of moving mitochondria (Panel d) were quantified (per 200 seconds and 100 μm). n=20 to 25 cells isolated from three different mice in each condition. *P<0.05; ***P<0.0001. One-way ANOVA

It was further discovered that TSA or tubastatin A treatment significantly increased the motor performance of HSPB1$^{S135F}$-expressing mice (P<0.0001; FIG. 8G). Treatment with either drug also increased electrophysiological parameters such as CMAP amplitudes as well as SNAP amplitudes (FIGS. 8H and 8I). It was also observed that the loss of acetylcholine-receptor clusters at the end plates in gastrocnemius muscle was restored (FIG. 9, Panel a) and that the level of denervation of the remaining neuromuscular junctions was decreased (FIG. 9, Panel b). These observations indicate that increasing acetylated α-tubulin abundance in peripheral nerves leads to re-innervation of muscles.

Finally, we measured ex vivo axonal transport in DRG neurons isolated from treated mice. In contrast to TSA, tubastatin A increased the total number of mitochondria (FIG. 9, Panel c). Moreover, the number of moving mitochondria was increased significantly after TSA or tubastatin A treatment (P<0.0001; FIG. 9, Panel d). Tubastatin A was more effective than TSA and resulted in a complete rescue of mitochondrial motility (FIG. 9, Panels c and d).

REFERENCES

1. Barisic N. et al. Charcot-Marie-Tooth disease: a clinico-genetic confrontation. *Ann. Hum. Genet.* 72:416-441 (2008).
2. Zuchner S. and J. M. Vance. Mechanisms of disease: a molecular genetic update on hereditary axonal neuropathies. *Nat. Clin. Pract. Neurol.* 2:45-53 (2006).
3. Evgrafov O. V. et al. Mutant small heat-shock protein 27 causes axonal Charcot-Marie-Tooth disease and distal hereditary motor neuropathy. *Nat. Genet.* 36:602-606 (2004).
4. Ismailov S. M. et al. A new locus for autosomal dominant Charcot-Marie-Tooth disease type 2 (CMT2F) maps to chromosome 7q11-q21. *Eur. J. Hum. Genet.* 9:646-650 (2001).
5. Arrigo A. P. The cellular "networking" of mammalian Hsp27 and its functions in the control of protein folding, redox state and apoptosis. *Adv. Exp. Med. Biol.* 594:14-26 (2007).
6. Dierick I., J. Irobi, P. De Jonghe, and V. Timmerman. Small heat shock proteins in inherited peripheral neuropathies. *Ann. Med.* 37:413-422 (2005).

7. Xanthoudakis S. and D. W. Nicholson. Heat-shock proteins as death determinants. *Nat. Cell Biol.* 2:E163-165 (2000).
8. Houlden H. et al. Mutations in the HSP27 (HSPB1) gene cause dominant, recessive, and sporadic distal HMN/CMT type 2. Neurology 71:1660-1668 (2008).
9. Ikeda Y. et al. A clinical phenotype of distal hereditary motor neuronopathy type II with a novel HSPB1 mutation. *J. Neurol. Sci.* 277:9-12 (2009).
10. James P. A., J. Rankin, and K. Talbot. Asymmetrical late onset motor neuropathy associated with a novel mutation in the small heat shock protein HSPB1 (HSP27). *J. Neurol. Neurosurg. Psychiatry* 79:461-463 (2008).
11. Kijima K. et al. Small heat shock protein 27 mutation in a Japanese patient with distal hereditary motor neuropathy. *J. Hum. Genet.* 50:473-476 (2005).
12. Ackerley S. et al. A mutation in the small heat-shock protein HSPB1 leading to distal hereditary motor neuronopathy disrupts neurofilament assembly and the axonal transport of specific cellular cargoes. *Hum. Mol. Genet.* 15:347-354 (2006).
13. Zhai J., H. Lin, J. P. Julien, and W. W. Schlaepfer. Disruption of neurofilament network with aggregation of light neurofilament protein: a common pathway leading to motor neuron degeneration due to Charcot-Marie-Tooth disease-linked mutations in NFL and HSPB1. *Hum. Mol. Genet.* 16:3103-3116 (2007).
14. Hamers F. P., G. C. Koopmans, and E. A. Joosten. Cat-Walk-assisted gait analysis in the assessment of spinal cord injury. *J. Neurotrauma* 23:537-548 (2006).
15. Vandeputte C. et al. Automated quantitative gait analysis in animal models of movement disorders. *BMC Neurosci.* 11:92 (2010).
16. Hollenbeck P. J. and W. M. Saxton. The axonal transport of mitochondria. *J. Cell Sci.* 118:5411-5419 (2005).
17. Westermann S. and K. Weber. Post-translational modifications regulate microtubule function. *Nat. Rev. Mol. Cell Biol.* 4:938-947 (2003).
18. Hammond J. W., D. Cai, and K. J. Verhey. Tubulin modifications and their cellular functions. *Curr. Opin. Cell Biol.* 20:71-76 (2008).
19. Chen S., G. C. Owens, H. Makarenkova, and D. B. Edelman. HDAC6 regulates mitochondrial transport in hippocampal neurons. *PLoS One* 5:e10848 (2010).
20. Gardiner J., D. Barton, J. Marc, and R. Overall. Potential role of tubulin acetylation and microtubule-based protein trafficking in familial dysautonomia. *Traffic* 8:1145-1149 (2007).
21. Hempen B. and J. P. Brion. Reduction of acetylated alpha-tubulin immunoreactivity in neurofibrillary tangle-bearing neurons in Alzheimer's disease. *J. Neuropathol. Exp. Neurol.* 55:964-972 (1996).
22. Hubbert C. et al. HDAC6 is a microtubule-associated deacetylase. *Nature* 417:455-458 (2002).
23. Zhang Y. et al. HDAC-6 interacts with and deacetylates tubulin and microtubules in vivo. *EMBO. J.* 22:1168-1179 (2003).
24. Haggarty S. J., K. M. Koeller, J. C. Wong, C. M. Grozinger, and S. L. Schreiber. Domain-selective small-molecule inhibitor of histone deacetylase 6 (HDAC6)-mediated tubulin deacetylation. *Proc. Natl. Acad. Sci. U.S.A.* 100:4389-4394 (2003).
25. Avila A. M. et al. Trichostatin A increases SMN expression and survival in a mouse model of spinal muscular atrophy. *J. Clin. Invest.* 117:659-671 (2007).
26. Dierick I. et al. Relative contribution of mutations in genes for autosomal dominant distal hereditary motor neuropathies: a genotype-phenotype correlation study. *Brain* 131:1217-1227 (2008).
27. Detmer S. A., C. Vande Velde, D. W. Cleveland, and D. C. Chan. Hind limb gait defects due to motor axon loss and reduced distal muscles in a transgenic mouse model of Charcot-Marie-Tooth type 2A. *Hum. Mol. Genet.* 17:367-375 (2008).
28. Cartoni R. et al. Expression of mitofusin 2(R94Q) in a transgenic mouse leads to Charcot-Marie-Tooth neuropathy type 2A. *Brain* 133:1460-1469 (2010).
29. Dequen F. et al. Reversal of neuropathy phenotypes in conditional mouse model of Charcot-Marie-Tooth disease type 2E. *Hum. Mol. Genet.* 19:2616-2629 (2010).
30. De Vos K. J., A. J. Grierson, S. Ackerley, and C. C. Miller. Role of axonal transport in neurodegenerative diseases. *Annu. Rev. Neurosci.* 31:151-173 (2008).
31. Baloh R. H., R. E. Schmidt, A. Pestronk, and J. Milbrandt. Altered axonal mitochondrial transport in the pathogenesis of Charcot-Marie-Tooth disease from mitofusin 2 mutations. *J. Neurosci.* 27:422-430 (2007).
32. de Brito O. M. and L. Scorrano. Mitofusin 2 tethers endoplasmic reticulum to mitochondria. *Nature* 456:605-610 (2008).
33. Niemann A., M. Ruegg, V. La Padula, A. Schenone, and U. Suter. Ganglioside-induced differentiation associated protein 1 is a regulator of the mitochondrial network: new implications for Charcot-Marie-Tooth disease. *J. Cell. Biol.* 170:1067-1078 (2005).
34. Tradewell M. L., H. D. Durham, W. E. Mushynski, and B. J. Gentil. Mitochondrial and axonal abnormalities precede disruption of the neurofilament network in a model of charcot-marie-tooth disease type 2E and are prevented by heat shock proteins in a mutant-specific fashion. *J. Neuropathol. Exp. Neurol.* 68:642-652 (2009).
35. Friedman J. R., B. M. Webster, D. N. Mastronarde, K. J. Verhey, and G. K. Voeltz. ER sliding dynamics and ER-mitochondrial contacts occur on acetylated microtubules. *J. Cell. Biol.* 190:363-375 (2010).
36. Janke C. and M. Kneussel. Tubulin post-translational modifications: encoding functions on the neuronal microtubule cytoskeleton. *Trends Neurosci.* 33:362-372 (2010).
37. Chuang D. M., Y. Leng, Z. Marinova, H. J. Kim, and C. T. Chiu. Multiple roles of HDAC inhibition in neurodegenerative conditions. *Trends Neurosci* 32:591-601 (2009).
38. Kazantsev A. G. and L. M. Thompson. Therapeutic application of histone deacetylase inhibitors for central nervous system disorders. *Nat. Rev. Drug Discov.* 7:854-868 (2008).
39. Rivieccio M. A. et al. HDAC6 is a target for protection and regeneration following injury in the nervous system. *Proc. Natl. Acad. Sci. U.S.A.* 106:19599-19604 (2009).
40. Dompierre J. P. et al. Histone deacetylase 6 inhibition compensates for the transport deficit in Huntington's disease by increasing tubulin acetylation. *J. Neurosci.* 27:3571-3583 (2007).
41. Kernochan L. E. et al. The role of histone acetylation in SMN gene expression. *Hum. Mol. Genet.* 14:1171-1182 (2005).
42. Dietz K. C. and P. Casaccia. HDAC inhibitors and neurodegeneration: at the edge between protection and damage. *Pharmacol. Res.* 62:11-17 (2010).
43. Choudhary C. et al. Lysine acetylation targets protein complexes and co-regulates major cellular functions. *Science* 325:834-840 (2009).

44. Krishnan J. et al. Over-expression of Hsp27 does not influence disease in the mutant SOD1(G93A) mouse model of amyotrophic lateral sclerosis. *J. Neurochem.* 106: 2170-2183 (2008).
45. Vanden Berghe P., G. W. Hennig, and T. K. Smith. Characteristics of intermittent mitochondrial transport in guinea pig enteric nerve fibers. *Am. J. Physiol. Gastrointest. Liver Physiol.* 286:G671-682 (2004).
46. Butler K. V., J. Kalin, C. Brochier, G. Vistoli, B Langley, and A. P. Kozikowski. Rational design and simple chemistry yield a superior, neuroprotective HDAC6 inhibitor, tubastatin A. *J. Am. Chem. Soc.* 132 (31):10842-6 (2010).
47. d'Ydewalle C., J. Krishnan, D. M. Chiheb, P. Van Damme, K. Irobi, A. P. Kozikowski, P. Vanden Berghe, V. Timmerman, W. Robberecht, and L. Van Den Bosch. HDAC6 inhibitors reverse axonal loss in a mouse model of mutant HSPB1-induced Charcot-Marie-Tooth disease. *Nat. Med.* 17(8):968-74 (2011).

What is claimed is:

1. A method of improving steppage gait in a subject suffering from Charcot-Marie-Tooth disease with impaired steppage gait, wherein the Charcot-Marie-Tooth disease is characterized by a mutation in the alpha-crystallin domain of 27 kDa small heat-shock protein 1 (HSPB1), the method comprising:

administering 25 mg/kg bodyweight of tubastatin A to the subject in need thereof to increase the electrophysiological parameters including compound muscle action potential (CMAP) amplitudes and sensory nerve action potential (SNAP) amplitudes, thereby improving steppage gait in the subject.

2. The method according to claim 1, wherein the alpha-crystallin domain mutation of HSPB1 is S135F.

* * * * *